US012678361B2

(12) United States Patent
Moosmann et al.

(10) Patent No.: US 12,678,361 B2
(45) Date of Patent: Jul. 14, 2026

(54) HEAD STABILIZATION SYSTEM AND METHOD WITH CASSETTE FEATURES

(71) Applicant: Black Forest Medical GmbH, Freiburg Im Breisgau (DE)

(72) Inventors: Severin Moosmann, Friesenheim (DE); Matthias E. Schuele, Freiburg (DE)

(73) Assignee: Black Forest Medical GmbH (DE)

( * ) Notice: Subject to any disclaimer, the term of this patent is extended or adjusted under 35 U.S.C. 154(b) by 0 days.

(21) Appl. No.: 18/731,583

(22) Filed: Jun. 3, 2024

(65) Prior Publication Data

US 2024/0315905 A1 Sep. 26, 2024

Related U.S. Application Data

(63) Continuation of application No. 16/103,461, filed on Aug. 14, 2018, now Pat. No. 12,042,439.
(Continued)

(51) Int. Cl.
*A61G 13/12* (2006.01)
*A61B 17/00* (2006.01)
(Continued)

(52) U.S. Cl.
CPC .......... *A61G 13/1285* (2013.01); *A61B 90/14* (2016.02); *A61G 13/121* (2013.01);
(Continued)

(58) Field of Classification Search
CPC .............. A61G 13/1285; A61G 13/121; A61G 13/1265; A61G 13/127; A61G 13/12;
(Continued)

(56) References Cited

U.S. PATENT DOCUMENTS 3,672,364 A 6/1972 Rankin
4,108,426 A 8/1978 Lindstroem et al.
(Continued)

FOREIGN PATENT DOCUMENTS

AU 3133495 2/1996
CN 1133157 A 10/1996
(Continued)

OTHER PUBLICATIONS

International Search Report and Written Opinion dated Oct. 11, 2019 for Application No. PCT/IB2019/000497, 16 pages.
(Continued)

*Primary Examiner* — Daniel A Miller
(74) *Attorney, Agent, or Firm* — FBT Gibbons LLP

(57) ABSTRACT

Exemplary head stabilization devices or head fixation devices (HFDs) for supporting and stabilizing a head of a patient during a medical procedure include a positioning assembly defining an axis of rotation. The positioning assembly includes a selectively rotatable portion that is rotatable about the axis of rotation to adjust a rotational position of the rotatable portion of the positioning assembly relative to the head of the patient. Also included is a head support configured to directly or indirectly adjustably connect with the positioning assembly such that the head support is translatable relative to the positioning assembly and rotatable in unison with the rotatable portion of the positioning assembly. The translation and rotation of the head support permits changing a position of the head support relative to the head of the patient.

18 Claims, 18 Drawing Sheets

Related U.S. Application Data

(60) Provisional application No. 62/662,855, filed on Apr. 26, 2018, provisional application No. 62/545,785, filed on Aug. 15, 2017.

(51) Int. Cl.
*A61B 90/00* (2016.01)
*A61B 90/14* (2016.01)

(52) U.S. Cl.
CPC ....... *A61G 13/1265* (2013.01); *A61G 13/127* (2013.01); *A61B 2017/00199* (2013.01); *A61B 2017/00221* (2013.01); *A61B 2090/065* (2016.02); *A61B 2090/0807* (2016.02); *A61B 2090/0811* (2016.02); *A61B 2090/0813* (2016.02); *A61G 2203/32* (2013.01); *A61G 2203/34* (2013.01)

(58) Field of Classification Search
CPC .......... A61G 13/1295; A61G 2203/032; A61G 2203/034; A61G 2013/0054; A61B 90/14; A61B 90/57; A61B 2090/065; A61B 2090/0807; A61B 2090/0811; A61B 2090/0813; A61B 2017/00199; A61B 2017/00221; A61B 2017/2945; A61B 17/2927; A61B 17/1285; A61B 17/0293; A61B 17/0469; A61B 17/062; A61B 17/064; A61B 17/12
USPC ................................................. 128/845, 847
See application file for complete search history.

(56) References Cited

U.S. PATENT DOCUMENTS

| | | | |
|---|---|---|---|
| 4,321,718 A | 3/1982 | Chern | |
| 4,545,572 A | 10/1985 | Day | |
| 5,009,318 A | 4/1991 | Lepinoy | |
| 5,154,186 A | 10/1992 | Laurin et al. | |
| 5,311,882 A | 5/1994 | Gagne | |
| 5,577,998 A | 11/1996 | Johnson, Jr. et al. | |
| 5,676,509 A | 10/1997 | Enzu | |
| 5,920,915 A | 7/1999 | Bainbridge | |
| 6,139,106 A | 10/2000 | Aldridge | |
| 6,226,820 B1 | 5/2001 | Navarro | |
| 6,355,049 B1 | 3/2002 | Gill | |
| 6,557,195 B2 | 5/2003 | Dinkler | |
| 6,594,839 B1 | 7/2003 | Papay | |
| 7,117,551 B1 | 10/2006 | Dinkler, II | |
| 7,213,883 B2 | 5/2007 | Chamitski | |
| 7,730,563 B1 * | 6/2010 | Sklar | A61G 13/121 5/640 |
| 7,797,773 B1 | 9/2010 | Wilk | |
| 2002/0032927 A1 | 3/2002 | Dinkler | |
| 2002/0042618 A1 | 4/2002 | Tweardy | |
| 2002/0151907 A1 | 10/2002 | Day | |
| 2003/0051293 A1 | 3/2003 | Chapman et al. | |
| 2004/0097985 A1 | 5/2004 | Lincoln | |
| 2004/0260311 A1 | 12/2004 | Bourel et al. | |
| 2006/0123548 A1 | 6/2006 | Heath | |
| 2006/0267392 A1 | 11/2006 | Chamitski et al. | |
| 2008/0072381 A1 | 3/2008 | Rolfes et al. | |
| 2008/0077151 A1 | 3/2008 | Kring | |
| 2009/0306662 A1 | 12/2009 | Dinkler | |
| 2010/0059064 A1 * | 3/2010 | Schule | A61B 90/14 128/845 |
| 2010/0078034 A1 | 4/2010 | Fischer et al. | |
| 2010/0307509 A1 | 12/2010 | King et al. | |
| 2013/0019877 A1 | 1/2013 | Sklar | |
| 2014/0135765 A1 | 5/2014 | Schuele et al. | |
| 2014/0275987 A1 | 9/2014 | Bzostek et al. | |
| 2015/0238117 A1 * | 8/2015 | Fielder | G01R 33/34046 5/637 |
| 2015/0327937 A1 | 11/2015 | Schuele | |
| 2015/0328035 A1 | 11/2015 | Idowu et al. | |
| 2016/0028796 A1 | 1/2016 | Garcia et al. | |
| 2016/0106508 A1 | 4/2016 | Lathrop et al. | |
| 2016/0151224 A1 | 6/2016 | Ferro et al. | |
| 2016/0175178 A1 | 6/2016 | Charles | |
| 2016/0228280 A1 | 8/2016 | Schuele et al. | |
| 2016/0324592 A1 | 11/2016 | Schuele | |
| 2017/0014201 A1 | 1/2017 | Grotenhuis et al. | |
| 2019/0053871 A1 | 2/2019 | Moosmann et al. | |
| 2019/0328035 A1 | 10/2019 | Cieslikowski et al. | |
| 2019/0328478 A1 | 10/2019 | Schuele | |

FOREIGN PATENT DOCUMENTS

| | | |
|---|---|---|
| CN | 103517730 A | 1/2014 |
| CN | 204562489 U | 8/2015 |
| CN | 105125286 | 12/2015 |
| CN | 103857433 A | 4/2016 |
| EP | 1009284 | 1/2004 |
| EP | 2014251 | 1/2009 |
| EP | 2010113 B1 | 7/2012 |
| ES | 1105831 U | 4/2014 |
| GB | 2094590 A | 9/1982 |
| GB | 2262435 A | 6/1993 |
| JP | S 52-125388 U | 9/1977 |
| JP | 2002-032927 A | 1/2002 |
| JP | 2002-536119 A | 10/2002 |
| JP | 2003-529436 A | 10/2003 |
| JP | 2004-509703 A | 4/2004 |
| JP | 2010-523269 A | 7/2010 |
| JP | 2013-517915 A | 5/2013 |
| JP | 2013-526970 A | 6/2013 |
| JP | 2020-531121 A | 5/2020 |
| WO | WO 1999/029252 | 6/1999 |
| WO | WO 2012/076199 | 6/2012 |
| WO | WO 2014/033542 A1 | 3/2014 |
| WO | WO 2016/028796 | 2/2016 |
| WO | WO 2017/089457 | 6/2017 |
| WO | WO 2019/034933 | 2/2019 |
| WO | WO 2019/034935 | 2/2019 |
| WO | WO 2020/065399 | 4/2020 |

OTHER PUBLICATIONS

International Search Report and Written Opinion dated Apr. 9, 2019 for Application No. PCT/IB2018/001018, 19 pages.
International Search Report and Written Opinion dated Jan. 3, 2019 for Application No. PCT/IB2018/001027, 11 pages.
International Invitation to Pay Additional Fees; Communication Relating to the Results of the Partial International Search; and Provisional Opinion Accompanying the Partial Search Result, dated Jan. 3, 2019 for Application No. PCT/IB2018/001018, 13 pages.
U.S. Appl. No. 16/103,461, filed Aug. 14, 2018.
Chinese Third Office Action for CN 201880067034.9 mailed Jan. 17, 2024.
European extended Search Report for EP 24208735.1 mailed Jan. 23, 2025.
JP Notice of Reasons for Refusal for JP 2023-040189 mailed Feb. 2, 2024.

* cited by examiner

HEAD STABILIZATION SYSTEM AND METHOD WITH CASSETTE FEATURES

PRIORITY

This application is a continuation of U.S. patent application Ser. No. 16/103,461, entitled "Head Stabilization System and Method with Cassette Features," filed Aug. 14, 2018, which claims priority to U.S. Provisional Patent Application No. 62/662,855, entitled "Head Stabilization System and Method with Cassette Features," filed Apr. 26, 2018, and U.S. Provisional Patent Application No. 62/545, 785, entitled "Non-Invasive Head Fixation Device with Conforming Pads," filed Aug. 15, 2017, the disclosures of which are incorporated by reference herein.

BACKGROUND

The systems and methods disclosed pertain to the field of patient stabilization, and in particular head and neck stabilization using stabilization devices known as head stabilization devices which are also referred to as head fixation devices (hereinafter referred to as "HFDs" or "HFD" in singular). HFDs are sometimes used during a variety of surgical and other medical procedures, for example during head or neck surgery or testing where it would be desirable to securely support a patient's head in a certain position. Because a patient may need to be positioned in a certain way for procedure or preference reasons, not all HFDs may be best-suited to provide the necessary patient stabilization. While a variety of stabilization devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

Figure 1:
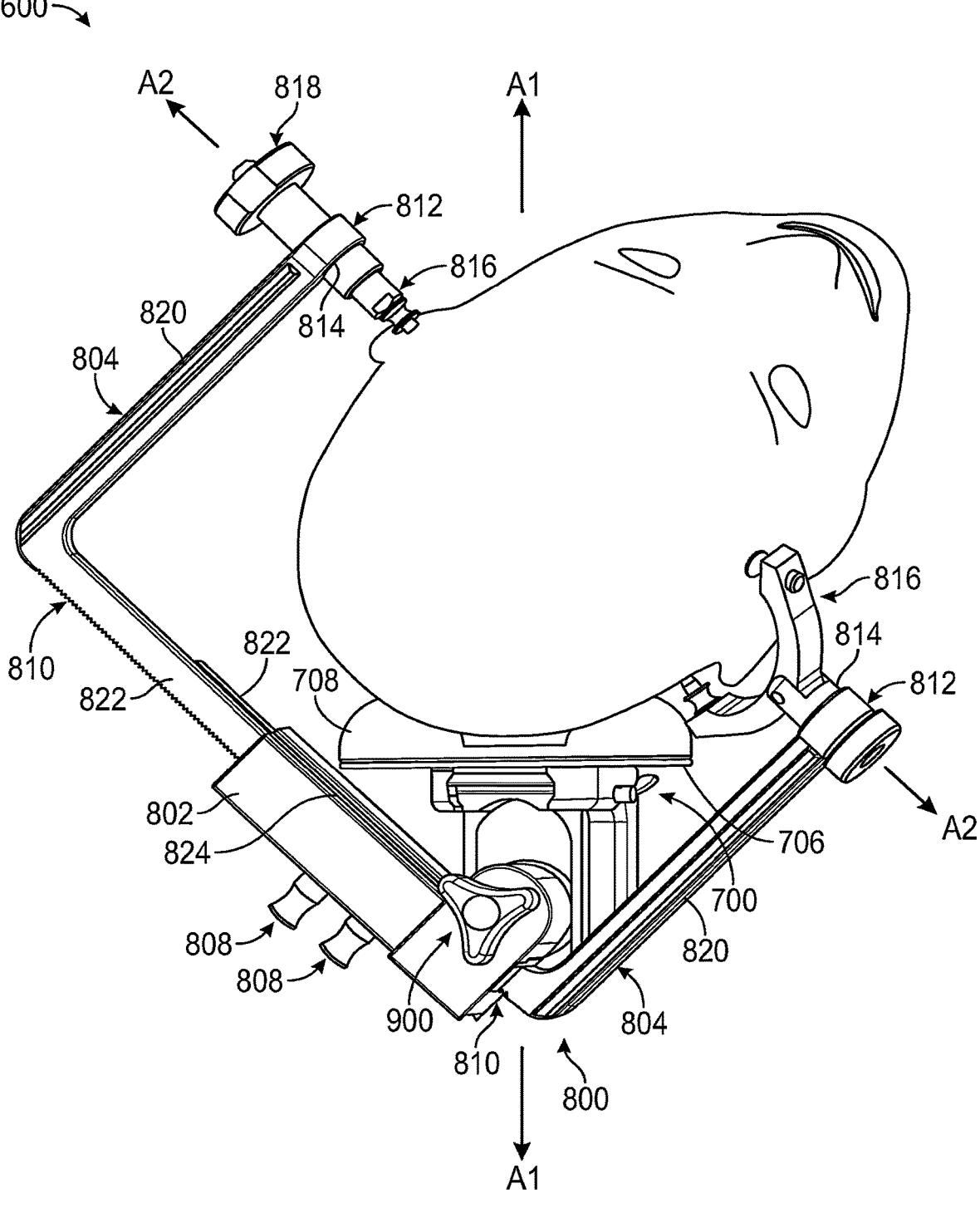
FIG. 1 depicts a perspective view of an exemplary HFD having cassette features.
Figure 2:
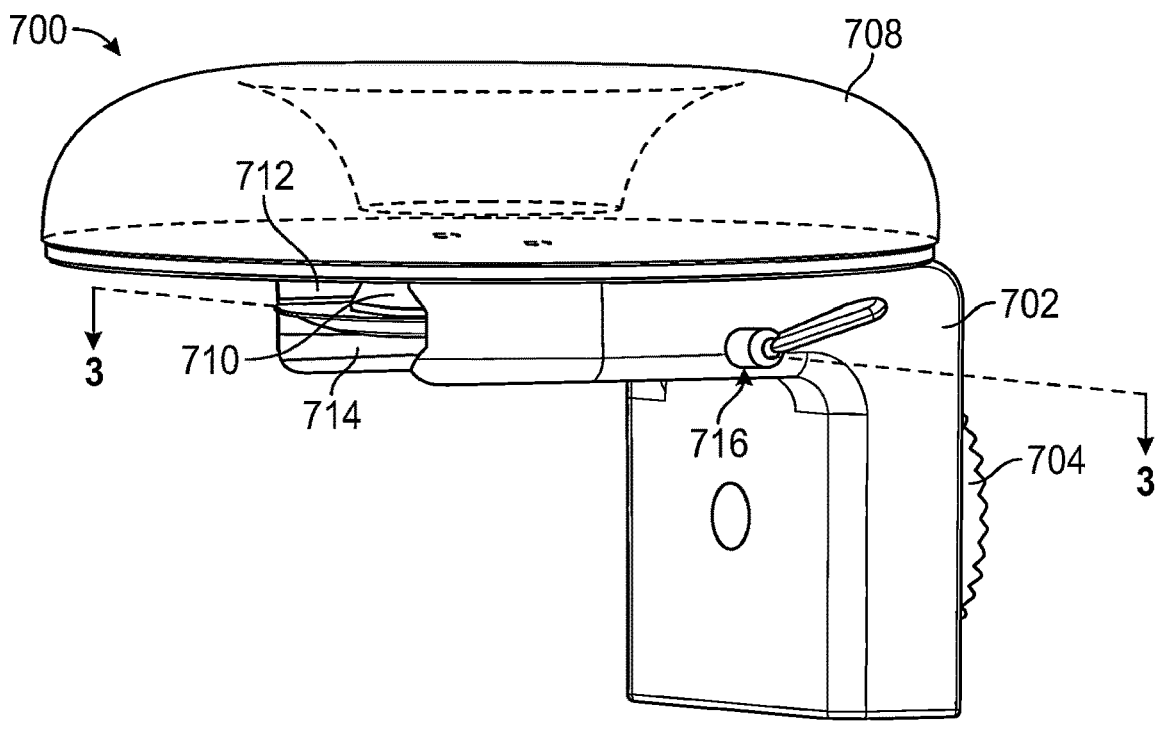
FIG. 2 depicts a partial perspective view of the HFD of FIG. 1, showing a central head support of the HFD.
Figure 3:
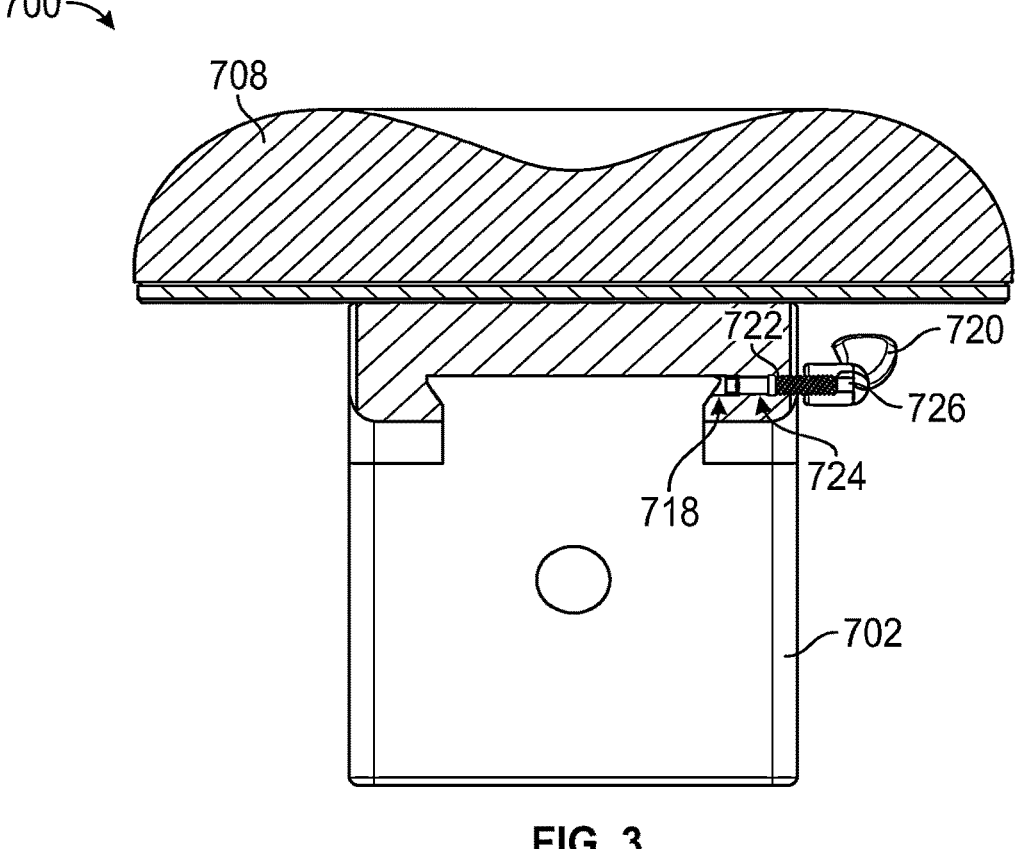
FIG. 3 depicts a front view of the HFD of FIG. 2 in cross section taken along the line 3-3 of FIG. 2.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description. As will be realized, the invention is capable of other different and obvious aspects, all without departing from the invention. Accordingly, the drawings and descriptions should be regarded as illustrative in nature and not restrictive.

I. Exemplary HFD

During certain medical procedures, it may be necessary or desirable to stabilize a patient's head using a HFD. It can be desirable to position the patient in a manner to provide the best access to the medical team and their equipment. This may involve the patient being in a prone position, in a supine position, or in an intermediate position where the patient's head is rotated left or right from the sagittal plane that defines a left side and a right side of the patient. When accommodating these and other positions for stabilizing a patient's head, adjustability of the HFD itself is a factor in stabilizing the patient securely so that movement or slippage of the patient's head is avoided. Referring now to the figures, FIGS. 1-5 illustrate an exemplary HFD (600) configured for use in supporting and stabilizing a head of a patient during a medical procedure. The HFD (600) comprises a central head support (700) and a skull clamp (800) connectable with the central head support (700) by a positioning assembly (900).

The central head support (700) comprises a body (702) and an attachment feature (704) on the body (702), where the attachment feature (704) is in the form of a starburst configured to connect with an operating table or other structure directly or indirectly via one or more intermediate structures. For example, in some instances a base unit, such as those available from pro med instruments GmbH, attaches to an operating table and the attachment feature (704) connects with the base unit. In some instances an adapter, such as a swivel adapter or other adapter available from pro med instruments GmbH, may connect with the base unit, and the attachment feature (704) of the central head support (700) connects with the adapter. In view of the teachings herein, various ways to connect the central head support (700) with a stable structure such as an operating table, etc. will be apparent to those of ordinary skill in the art.

The central head support (700) also comprises a base (706) that connects with the body (702) and that holds or retains a cushion (708). The cushion (708) may connect with the base (706) by way of an adhesive, mechanical fasteners such as screws or hook and loop, or other ways that will be apparent to those of ordinary skill in the art. In some versions, the cushion (708) is selectively connected with the base (706) such that the cushion (708) may be disposable or may be removed for cleaning and sterilization after use. The cushion (708) is configured to contact the head of the patient when the HFD (600) is used to support and stabilize the patient. In the present example, the base (706) connects with the body (702) by way of a disc (710), which is connected with the base (706) using fasteners such as screws or bolts, etc. The disc (710) is received within a slot (712) defined in the body (702). In the present example, the disc (710) is rotatable within the slot (712) such that the attached base (706) and cushion (708) are rotatably adjustable. In the present example, the disc (710) and slot (712) features and construction is the same or similar to those features as shown and described in accordance with the teachings in U.S. Pat. App. No. 62/662,874, entitled "Head Stabilization System and Method with Arc Features," filed on Apr. 26, 2018, the disclosure of which is incorporated by reference herein.

The cushion (708) is configured to contain a shape-conforming material, which may be a fluid such as liquid, gas, or gel. In one version, the shape-conforming material is one of either a gel, a foam, or a granule material. In view of the teachings herein, other shape-conforming materials usable with the cushion (708) will be apparent to those of ordinary skill in the art.

In use, the central head support (700) is configured to provide subjacent support to the head of the patient. In this manner, the central head support (700) defines a plane that extends subjacent to the head of the patient when the head of the patient is supported by the central head support. In the present example, the central head support (700) is positioned such that the plane defined by the central head support (700) is parallel to a floor, or orthogonal to a direction of gravitational force on the central head support (700). Furthermore, the central head support (700) defines a central axis (A1) that extends through the center of the cushion (708) and parallel with the direction of gravitation force on the central head support (700).

The positioning assembly (900) of the HFD (600) connects with the central head support (700). In the present example the positioning assembly (900) comprises a cassette carrier (902), a connector (904), an actuator (906), and a locking insert (908). In connecting with the central head support (700), the connector (904) includes a beam portion (910) that is slidingly received by a slot (714) of the central head support (700), which is located beneath the slot (712) that receives the disc (710). In this manner, the central head support (700) is configured to adjust the spacing between the central head support (700) and the positioning assembly (900). Since the positioning assembly (900) is further connected with the skull clamp (800) as will be described further below, the central head support (700) can be considered to be configured to adjust the spacing between itself and the skull clamp (800). The profile of the beam portion (910) has a complementary shape to the slot (714). In the present example the beam portion (910) and slot (714) together form a dovetail interface. In this manner the connector (904) is translatable along the slot (714), which adjusts the spacing between the positioning assembly (900) and the central head support (700).

To control the adjustability of the connector (904) within the slot (714), the central head support (700) comprises an actuator (716) that includes a lock feature (718) that contacts the beam portion (910) to either secure its position relative to the body (702) within the slot (714) via a compression engagement, or permit slidable adjustment of the connector (904) relative to the body (702) by the lock feature (718) disengaging from contacting the beam portion (910) at least sufficiently to permit translational movement of the connector (904). To control the contact of the lock feature (718) with the beam portion (910), the actuator (716) includes a lever (720) that is rotated. Rotation of the lever (720) causes the lock feature (718) to move toward or away from the beam portion (910) depending on the direction the lever (720) is rotated. The actuator (716) includes a threaded rod (722) that extends through a threaded bore (724) in the body (702) of the central head support (700). The lever (720) includes a threaded bore (726) that engages the threaded rod (722). The threaded rod (722) connects with the lock feature (718). Rotating the lever (720) rotates the threaded rod (722) such that the threaded rod (722) translates within the threaded bore (724) of the body (702) toward or away from the beam portion (910) based on the direction of rotation. The translation of the threaded rod (722) toward the beam portion (910) drives the lock feature (718) into contact with the beam portion (910) of the connector (904) to thereby secure the position of the connector (904) relative to the central head support (700). In a similar manner, translation of the threaded rod (722) away from the beam portion (910) moves the lock feature (718) away the beam portion (910) to permit adjustment of the connector (904). In the configuration described above, the adjustable movement of the connector (904) is along or parallel to the plane defined by the central head support (700). In view of the teachings herein, other ways to connect the positioning assembly (900) with the central head support (700) will be apparent to those of ordinary skill in the art.

The connector (904) of the positioning assembly (900) further connects with the cassette carrier (902). The connector (904) includes a slot (912) that is configured to receive a flange (914) of the cassette carrier (902). In the present example, a profile of flange (914) has a complementary shape to a profile of the slot (912). For instance, the flange (914) and slot (912) together form a dovetail interface. In this manner the cassette carrier (902) is translatable along the slot (912) of the connector (904), which thereby adjusts the spacing between the skull clamp (800) that connects with the cassette carrier (902) as discussed below, and the central head support (700).

The connection between the cassette carrier (902) and the connector (904) is further configured for rotational adjustment in addition to the translational adjustment mentioned above. For instance, the flange (914) of the cassette carrier (902) is rotatable within the slot (912) of the connector (904). This rotational movement allows for the cassette carrier (902) as well as the skull clamp (800) attached thereto as will be discussed below to be rotationally adjusted relative to the connector (904) and central head support (700) attached thereto as discussed above. Therefore, in the present example, the positioning assembly (900) is configured to provide for adjusting the skull clamp (800) relative to the central head support (700) rotationally as well as translationally. This allows for the skull clamp (800) to be raised and lowered relative to the central head support (700), and patient's head resting thereon. This also allows for the skull clamp (800) to be rotated about the patient's head resting upon the central head support (700). Moreover this dual adjustment is provided for in a single connection interface within the positioning assembly (900) between the cassette carrier (902) and the connector (904). In terms of the range of adjustability for rotation of the cassette carrier (902) with connected skull clamp (800) relative to the central head support (700), in the present version, the skull clamp (800) can be rotated in either direction up to about forty-five degrees offset from the central axis (A1) defined by the central head support (700). In view of the teachings herein, other ways to adjust the skull clamp (800) relative to the central head support (700) greater and lesser amounts or degrees will be apparent to those of ordinary skill in the art.

The positioning assembly (900) further incudes the actuator (906). The actuator (906) is configured to selectively secure the position, both rotational position and translational position, of the cassette carrier (902) with the connector (904). With the configuration described and illustrated, the actuator (906) is configured to selectively secure the position of the skull clamp (800), both rotational position and translational position, relative to the central head support (700). Moreover, the single actuator (906) is configured to selectively secure both these adjustments substantially simultaneously.

In the illustrated version, the actuator (906) comprises a threaded rod (916) connected with a knob (918). The cassette carrier (902) comprises a threaded bore (920) configured to receive the threaded rod (916) of the actuator (906). The threaded bore (920) extends all the way through the cassette carrier (902) from one side to the other. In the present example, the threaded bore (920) extends through the flange (914), with the end of the threaded rod (916) contacting the connector (904) within the slot (912).

Rotating the knob (918) of the actuator (906) translates the cassette carrier (902) toward or away from the connector (904) depending on the direction the knob (918) is rotated based on the threaded engagement between the threaded rod (916) and the threaded bore (920). By translating the cassette carrier (902) toward the connector (904), the flange (914) moves toward the connector (904) and a sufficient gap or space is created at the interface of the flange (914) and slot (912) of the connector (904) so that the cassette carrier (902) can be rotationally and translationally adjusted as described above. By using the actuator (906) to translate the cassette carrier (902) away from the connector (904), the flange (914) moves away from the connector (904) such that it contacts an inner wall (922) of the slot (912) creating an interference between the flange (914) and the slot (912) so that the flange (914) binds against the inner wall (922) of the slot (912) to secure the cassette carrier (902) relative to the connector (904). This secures both the rotational position as well as the translational position.

In the present example, rotation of the actuator (906) only requires minimal rotational movement to move the positioning assembly (900) from the adjustable to fixed states. For instance, by way of example only, and not limitation, in one version the positioning assembly (900) can be moved from an adjustable to a fixed state with as little as one quarter rotation of the knob (918) of the actuator (906). Of course in other versions, the positioning assembly (900) may be configured such that greater or less rotation of the actuator (906) may be used to move the positioning assembly (900) from an adjustable to a fixed state.

As shown in FIG. 1, the skull clamp (800) connects with the positioning assembly (900). More specifically, the skull clamp (800) connects with the positioning assembly (900) in such a manner that the skull clamp (800) is selectively moveable or adjustable relative to the positioning member (900). In the illustrated version, the cassette carrier (902) comprises a pair of sidewalls (924) that define a space (925) configured to receive a cassette (802) of the skull clamp (800). The cassette carrier (902), on each sidewall (924) includes an inward protrusion (926) sized such that the cassette (802) is held from beneath by the two protrusions (926). With this configuration, the cassette (802) is translatable relative to the cassette carrier (902) and the translation occurs along a longitudinal axis defined by the cassette (802). By moving or adjusting the skull clamp (800) relative to the positioning assembly (900) in this manner, since the positioning assembly (900) connects with the central head support (700), the position of the skull clamp (800) is adjustable relative to the central head support (700). Furthermore, as shown in FIG. 1 for example, it is possible to adjust the skull clamp (800) rotationally by up to at least about forty-five degrees offset from the central axis (A1), and also keep the skull clamp (800) centered about the cushion (708) of the central head support (700) by adjusting the position of the cassette (802) relative to the cassette carrier (902). Keeping the skull clamp (800) centered about the cushion (708) allows for a more stable stabilization of the patient's head resting upon the cushion (708).

Furthermore, when a patient's head is supported by the central head support (700), in at least some examples, movement of the skull clamp (800) rotationally—based on rotating the cassette carrier (902) relative to the connector (904)—and in combination translationally—based on translation of the cassette (802) relative to the cassette carrier (902)—alters a position of the skull clamp (800) concentrically, or substantially concentrically, about the head of the patient. In similar terms, a patient defines a sagittal plane that divides the patient into left and right sides, and an axis that extends longitudinally along the sagittal plane is considered a longitudinal axis defined by the patient. Generally this longitudinal axis extends from the head of the patient to the foot of the patient. In at least some examples, movement of the skull clamp (800) as described above alters a position of the skull clamp (800) about this longitudinal axis defined by the patient. As mentioned above, in some instances the skull clamp (800) is adjustable in either direction relative to the central head support (700) and the patient's longitudinal axis up to about forty-five degrees from the central axis (A1) defined by the central head support (700). In this manner, the HFD (600) permits semi-lateral positioning of the skull clamp (800) on either side of the head of the patient supported by the central head support (700) up to about forty-five degrees. In view of the teachings herein, modifications to the HFD (600) to achieve adjustments of greater than or less than about forty-five degrees will be apparent to those of ordinary skill in the art.

Turning now to further details of the skull clamp (800) as shown in FIG. 1, the skull clamp (800) comprises the cassette (802), and a pair of extension bars (804). The cassette (802) comprises a pair of openings (806) configured to receive the extension bars (804). The extension bars (804) are independently moveable relative to the cassette (802) and each other. Furthermore, the cassette (802) comprises a pair of locks (808) that are configured to engage a respective extension bar (804) to either secure the extension bar (804) in position or permit adjustment of the extension bar (804). In this manner, each extension bar (804) comprises a toothed rack (810) and each lock (808) comprises a complementary shaped toothed portion residing within the cassette (802) that is moveable to engage or disengage the toothed rack (810) with which it is associated. For instance, the locks (808) are initially biased by a spring or other structure such that the toothed portion will engage with the toothed rack (810) and thus lock or secure the position of the extension bar (804) relative to the cassette (802). Each lock (808) may be pulled downward or away from the cassette (802) to disengage the toothed portion of the lock (808) from the toothed rack (810) and thereby permit lateral movement of the extension bar (804) relative to the cassette (802) and the other extension bar (804). In this manner cassette (802) can be considered to be a locking member.

In the present example, the extension bars (804) are interchangeable such that one may replace the other in terms of its position within the cassette (802). Each extension bar (804) further comprises an upper end portion (812) having a bore (814) configured to receive a stabilizing assembly (816). The stabilizing assemblies (816) are configured to contact the head of the patient and provide lateral support and stabilization to the head of the patient. In the present example, the stabilizing assembly (816) may take the form of a single pin or a dual pin assembly. Furthermore, the stabilizing assembly (816) may include a torque screw (818) for adjusting the force or pressure applied to the patient's head by the stabilizing assemblies (816). In other versions, stabilizing assemblies (816) may take the form of a single or multi-chamber pad. Returning to the present example, each extension bar (804) comprises an upright portion (820) and a base (822) with the upright portion (820) defining a longitudinal axis. In the present example, each respective bore (814) is offset from the longitudinal axis defined by the upright portion (820) of each respective extension bar (804). Furthermore, when the extension bars (804) are positioned within the cassette (802) the bores (814) are offset in opposite directions such that they align and share a common axis (A2) that extends through each bore (814). Additionally, each of the extension bars (804) defines a rail configured to receive one or more accessories positionable along at least a portion of the extension bar (804).

Figures 7, 8:
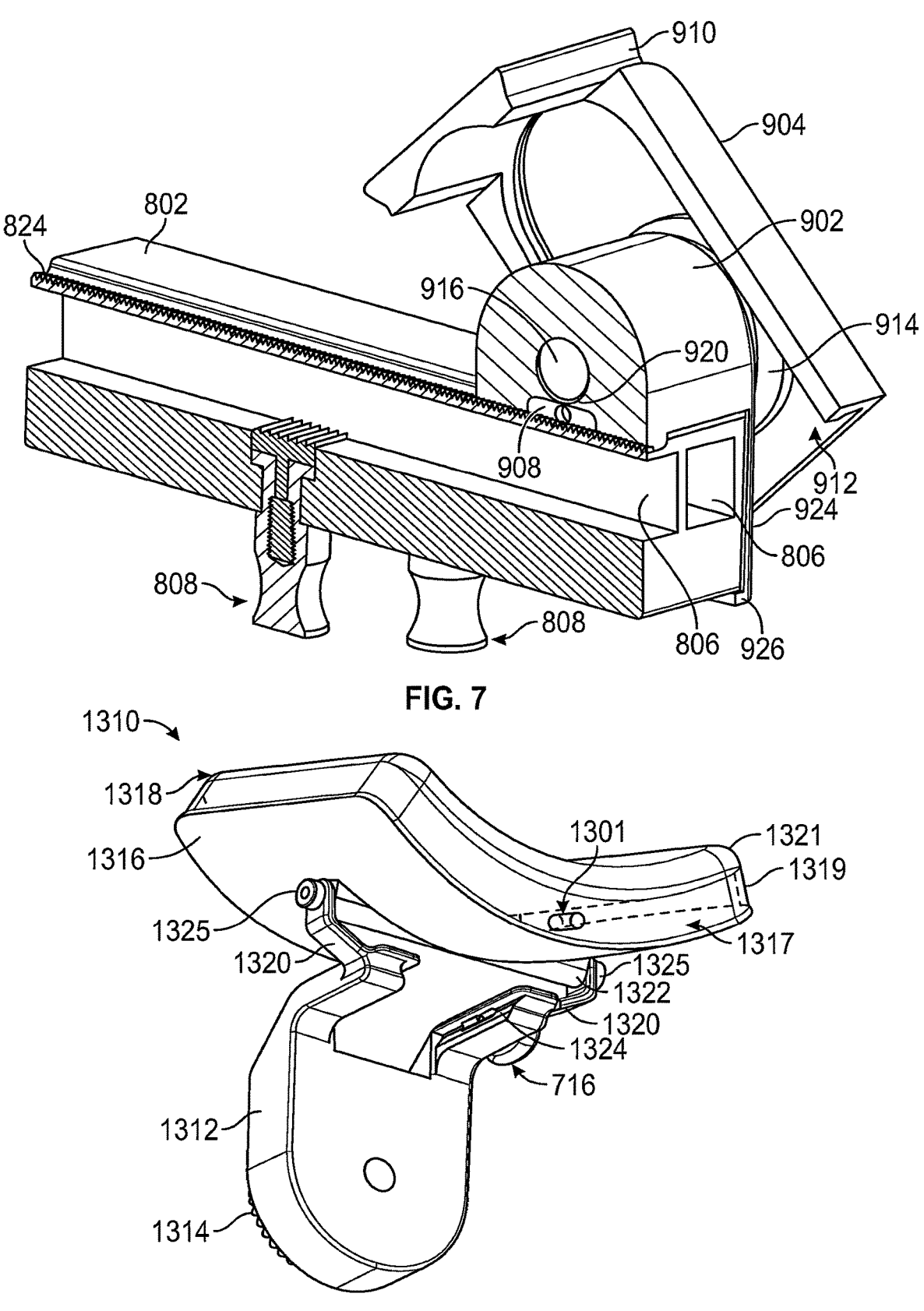
FIG. 7 depicts a cross section view taken along line 7-7 of FIG. 5.
FIG. 8 depicts a perspective view of another exemplary central head support usable with the HFD of FIG. 1.

As mentioned above, the cassette (802) of the skull clamp (800) is configured to selectively translate relative to the cassette carrier (902) of the positioning assembly (900). Referring to FIGS. 1 and 7, in the present example, the cassette (802) further comprises a toothed rack (824). The cassette carrier (902) further comprises a locking insert (908). The locking insert (908) comprises a toothed rack that complements, and is configured to selectively engage with, the toothed rack (824) of the cassette (802). When the locking insert (908) is in a disengaged position the cassette (802) can be translated relative to the cassette carrier (902). As described above, this translational movement provides for adjustment of the skull clamp (800) relative to the central head support (700). When the locking insert (908) is in an engaged position where its toothed rack engages with the toothed rack (824) of the cassette (802), the cassette (802) is fixed or secured relative to the cassette carrier (902). When secured, the skull clamp (800) is secured relative to the central head support (700) so that it cannot translate along the longitudinal axis of the cassette (802) relative to the positioning assembly (900).

Figure 4:
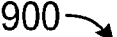
FIG. 4 depicts a partial perspective view of the HFD of FIG. 1, showing a positioning assembly of the HFD.
Figure 4:
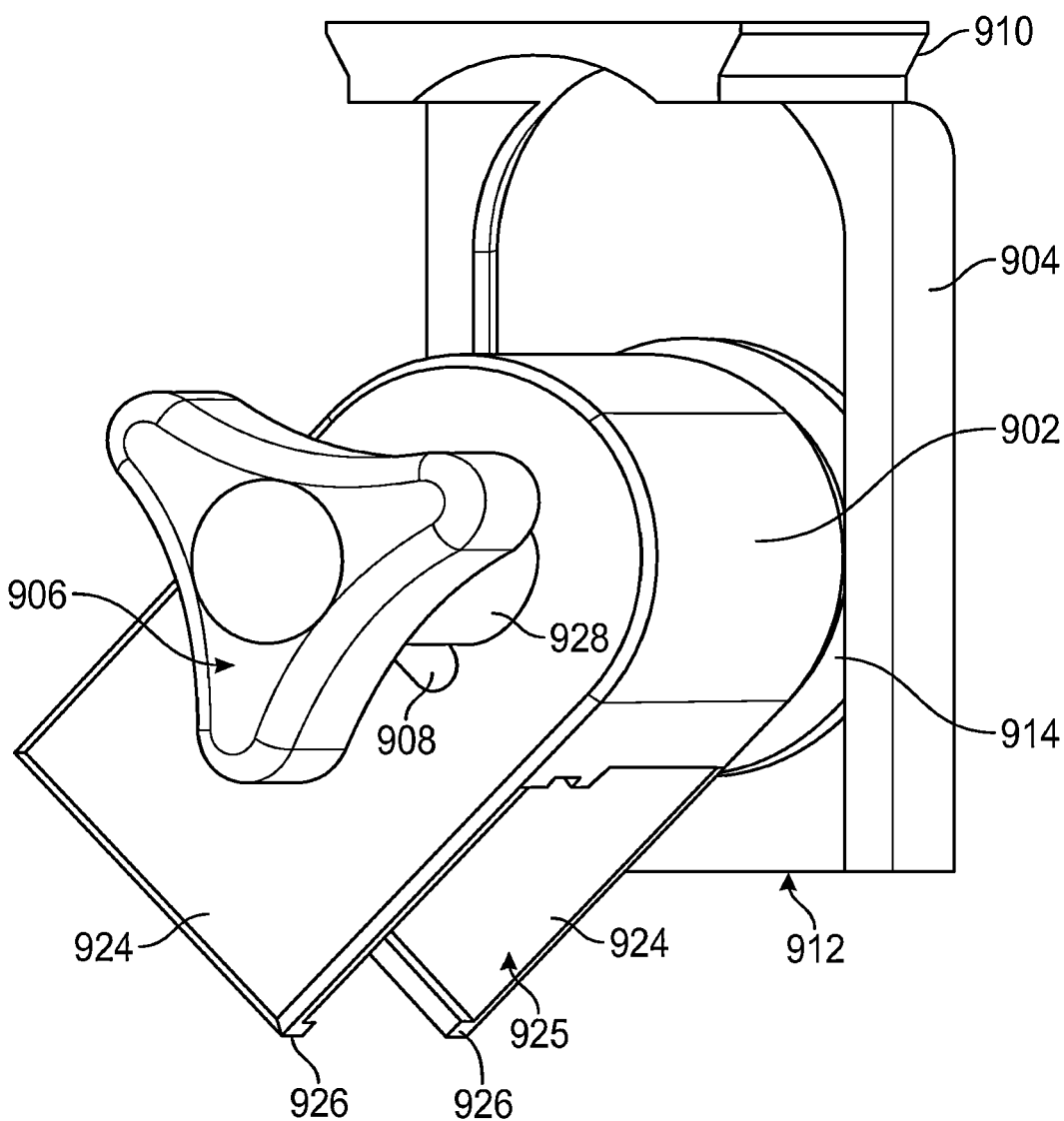
Figure 5:
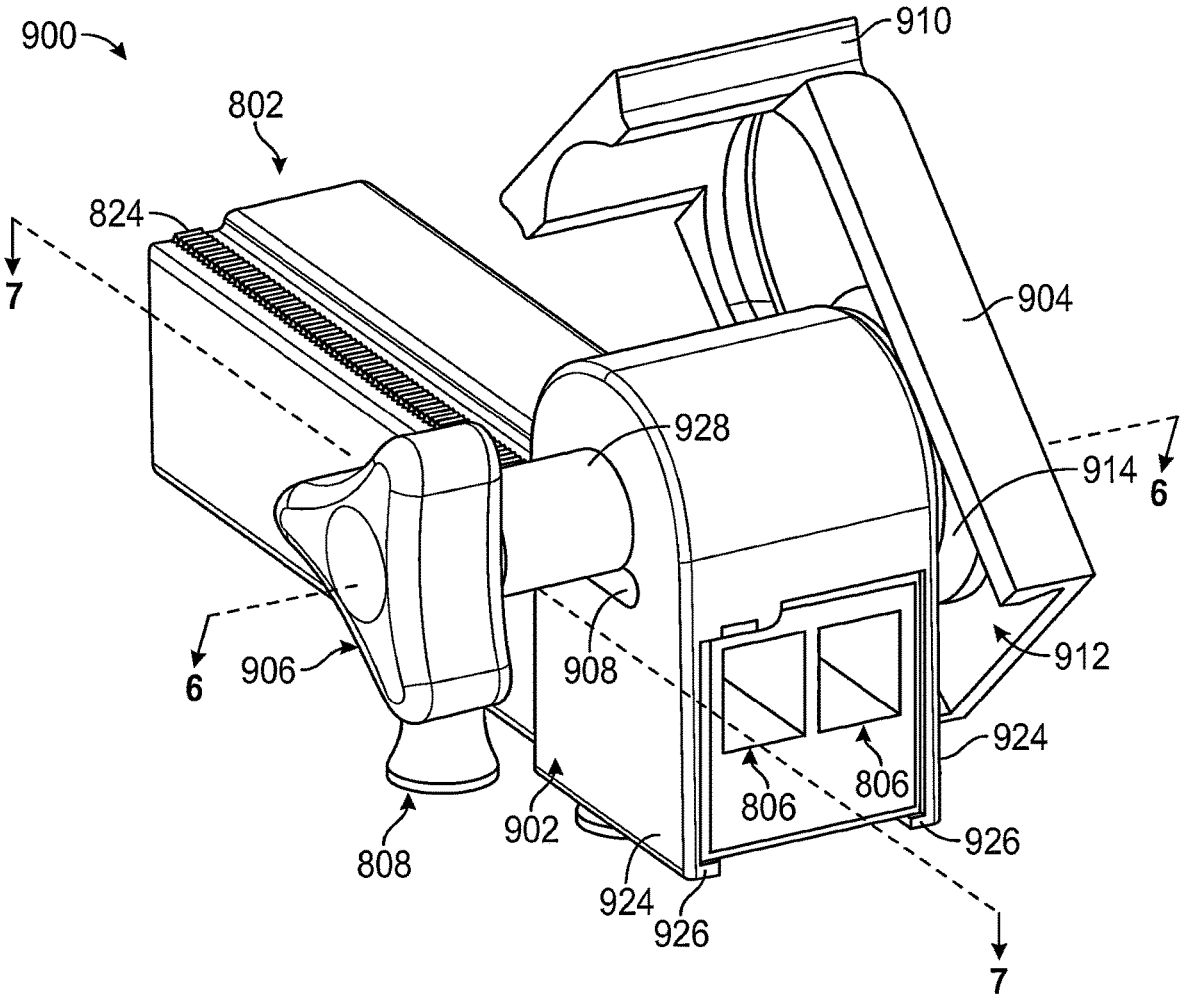
FIG. 5 depicts a partial perspective view of the positioning assembly of FIG. 4 connected with a portion of the skull clamp.
Figure 6:
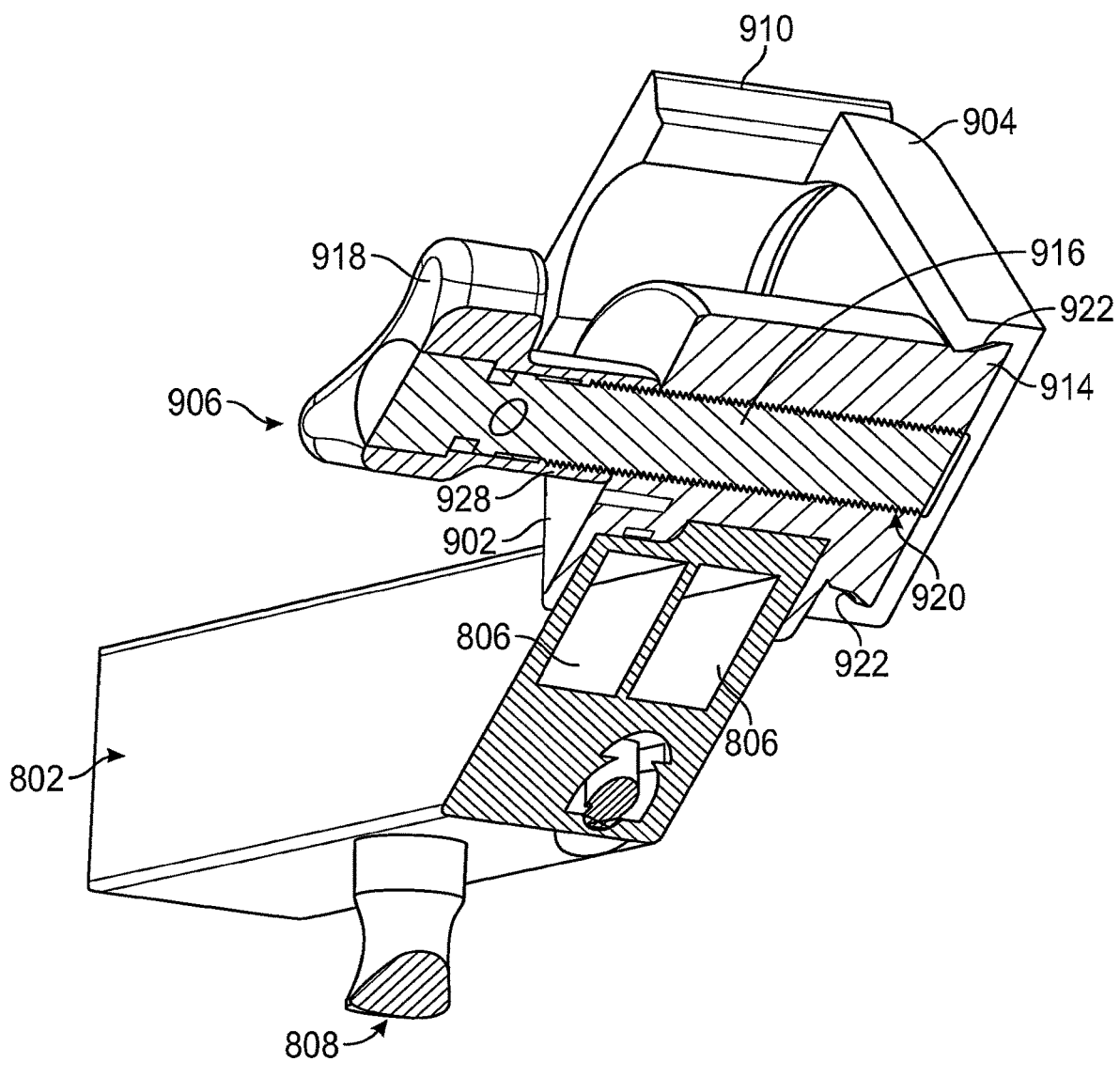
FIG. 6 depicts a cross section view taken along line 6-6 of FIG. 5.

Referring to FIGS. 4 and 5, the locking insert (908) is held in place with the cassette carrier (902) by an interference fit with a collar (928) of the actuator (906). In the present version, loosening the actuator (906) such that the position assembly (900) can be adjusted as discussed above, further loosens the interference fit between the collar (928) and the locking insert (908). Thus in this state, the locking insert (908) may slide outward, away from the space (925) defined by the sidewalls (924) of the cassette carrier (902). This movement of the locking insert (908) causes the toothed rack of the locking insert (908) to disengage from the toothed rack (824) of the cassette (802) so that the cassette (802) can be adjusted relative to the cassette carrier (902) as discussed above. When the actuator (906) is tightened such that the position assembly (900) is not adjustable as discussed above, the collar (928) of the actuator (906) pushes against the locking insert (908) so that the locking insert (908) is fully inserted or seated within the cassette carrier (902). In this state the toothed rack of the locking insert (908) engages the toothed rack (824) of the cassette (802) so that the cassette (802) is fixed or secured relative to the cassette carrier (902) as discussed above.

The above configuration describes and shows the adjustability of the skull clamp (800) relative to the central head support (700) via the rotation and translation of the flange (914) of the cassette carrier (902) within the slot (912) of the connector (904), and via the translation of the cassette (802) relative to the cassette carrier (902). Furthermore, in the present version, actuation of the single actuator (906) causes the HFD (600) to be in the adjustable state or fixed state depending on the mode of actuation. In this manner, the actuator (906) is operable to substantially simultaneously lock or unlock the HFD (600) for adjustment with respect to three different adjustments. In other versions such substantially simultaneous locking and unlocking adjustment capability is not required, and this may occur sequentially. Also in some other versions, the locking insert (908) may be removed or inserted within the cassette carrier (902) when the actuator (906) is backed out far enough from the cassette carrier (902) such that there is sufficient space between the collar (928) and the cassette carrier (902) within which to place and insert or remove the locking insert (908) from the cassette carrier (902). In view of the teachings herein, other ways to modify the actuator (906) and its operability will be apparent to those of ordinary skill in the art.

II. Exemplary Pressure Control Pivoting Cushion

In providing HFDs with ample adjustability to accommodate various patient positioning, another desirable feature can be to incorporate a selective pivot adjustment to the cushion of the HFD. Other features that can be incorporated into the cushion pertain to management or control of the contact pressure between the cushion and the patient. FIG. 8 depicts a central head support (1310) that can be used in place of the central head support (700) of the HFD (600). The central head support (1310) incorporates a pivoting cushion feature and features that aid in controlling contact pressure.

The central head support (1310) comprises a slot (1324) that receives the beam portion (910) of the connector (904) of the positioning assembly (900). The central head support (1310) further comprises a body (1312) and an attachment feature (1314) on the body (1312), where the attachment feature (1314) is in the form of a starburst configured to connect with an operating table or other structure directly or indirectly via one or more intermediate structures. For example, in some instances a base unit, such as those available from pro med instruments GmbH, attaches to an operating table and the attachment feature (1314) connects with the base unit. In some instances an adapter, such as a swivel adapter or other adapter available from pro med instruments GmbH, may connect with the base unit, and the attachment feature (1314) of the central head support (1310) connects with the adapter. In view of the teachings herein, various ways to connect the central head support (1310) with a stable structure such as an operating table, etc. will be apparent to those of ordinary skill in the art.

The central head support (1310) also comprises a base (1316) that connects with the body (1312) and that holds or retains a cushion (1318). The cushion (1318) may connect with the base (1316) by way of an adhesive, mechanical fasteners such as screws or hook and loop, or other ways that will be apparent to those of ordinary skill in the art. In some versions, the cushion (1318) is selectively connected with the base (1316) such that the cushion (1318) may be disposable or may be removed for cleaning and sterilization after use. The cushion (1318) is configured to contact the head of the patient when the HFD (600) is used to support and stabilize the patient. In the present example, the base (1316) connects with the body (1312) by way of a pair of arms (1320) that extend from the body (1312) outward and upward. The base (1316) comprises a connection member (1322) defining an axis extending transversely across the base (1316). The connection member (1322) comprises a pair of bores and each bore aligns with a respective bore in each of the arms (1320). The axis defined by the connection member (1322) extends along the bores of the connection member (1322) such that the axis defines a pivoting axis about which the base (1316) and connected cushion (1318) are pivotable. A pair of fasteners (1325) extend through the bores of the arms (1320) and engage the bores of the connection member (1322) to pivotably connect the base (1316) with the body (1312) of the central head support (1310). The fasteners (1325) may be tightened to secure the position of the base (1316) and connected cushion (1318), and conversely the fasteners (1325) may be loosened to permit pivotable adjustment of the base (1316) and connected cushion (1318).

In use, the central head support (1310) is configured to provide subjacent support to the head of the patient. In this manner, the central head support (1310) defines a plane that extends subjacent to the head of the patient when the head of the patient is supported by the central head support. In the present example, the central head support (1310) is positioned such that the plane defined by the central head support (1310) may be adjusted based on the pivoting action of the base (1316) and connected cushion (1318). Therefore, the plane defined by the central head support (1310) is not limited to being parallel to a floor, or orthogonal to a direction of gravitational force on the central head support (1310).

The central head support (1310) is configured to adjust a spacing between the central head support (1310) and positioning assembly (900) in the same manner as discussed above with respect to the central head support (700) and the positioning assembly (900). For instance, the connector (904) adjustably connects with the body (1312) of the central head support (1310). As illustrated, within the body (1312) is a slot (1324). The slot (1324) receives the beam portion (910) of the connector (904). The profile of the beam portion (910) has a complementary shape to the slot (1324). In the present example the beam portion (910) and slot (1324) together form a dovetail interface. In this manner the connector (904) is translatable along the slot (1324), which adjusts the spacing between the positioning assembly (900) and the central head support (1310). To control the adjustability of the connector (904) within the slot (1324), the central head support (1310) comprises the actuator (716) and the lock feature (718), which are configured and operable in the same manner as described above. In this configuration, the connector (904) is adjustable along or parallel to the plane defined by the central head support (1310) to change a position of the positioning assembly (900) relative to the central head support (1310).

The cushion (1318) comprises a first chamber (1319) having an internal space (1317) that is configured to be filled with a fluid. The fluid may be a gas or a liquid. The first chamber (1319) includes a port (1301) that is configured to provide access to the internal space (1317). The fluid may be directed to the internal space (1317) within the first chamber (1319) or extracted from or vented from the internal space (1317) of the first chamber (1319). When venting fluid from the first chamber (1319), all or a portion of the fluid may be released or vented from the internal space (1317).

The cushion (1318) further comprises a second chamber (1321), which is configured to be filled with a shape-conforming material. In the present example, the first chamber (1319) is positioned subjacent to the second chamber (1321). Furthermore, the second chamber (1321) is configured to contact the patient's head. In view of the teachings herein, it will be apparent to those of ordinary skill in the art that the relative positions of the first and second chambers (1319, 1321) may be switched in other versions. In one version, the shape-conforming material is one of either a gel, a foam, or a granule material. In view of the teachings herein, other shape-conforming materials usable with the cushion (1318) will be apparent to those of ordinary skill in the art.

With the configuration of the cushion (1318) described above, the cushion (1318) is configured to provide a uniform distribution of contact pressure with the head of the patient when the head is supported by the central head support (1310). Moreover, the contact pressure can be increased by filling the first chamber (1319) with fluid via the port (1301) when the system is configured for use with skull pins. Conversely, the contact pressure can be decreased by venting the fluid from the first chamber (1319) as mentioned above. By reducing the contact pressure, blood flow can be restored to the area of the patient's head in contact with the cushion (1318). In some instances, but not required in all versions, substantial venting of the fluid from the first chamber (1319) may cause the cushion (1318) to deflate or reduce in height such that the cushion (1318) no longer contacts the head of the patient or does not apply relevant pressure to the patient's head. Similar to above, by reducing the contact pressure to the extent that the contact pressure between the cushion (1318) and the patient is lacking, blood flow can be restored to this area of the patient's head that was stabilized with the cushion (1318). By reducing contact pressure and providing for restoration of blood flow, tissue trauma or injury can be avoided or the risk reduced. Additionally, stabilization can be maintained by the stabilization assemblies (816) when reducing contact pressure between the cushion (1318) and the patient's head so as to not sacrifice stabilization of the patient when restoring blood flow to an area of tissue. In some instances, once sufficient time has elapsed to restore blood flow to the tissue area in contact with the cushion (1318), the contact pressure can be increased again by filling the first chamber (1319) with the fluid to provide or restore an enhanced or a greater degree of stabilization.

III. Exemplary Non-Invasive Configuration with Multi-Chamber Cushion

Figure 9:
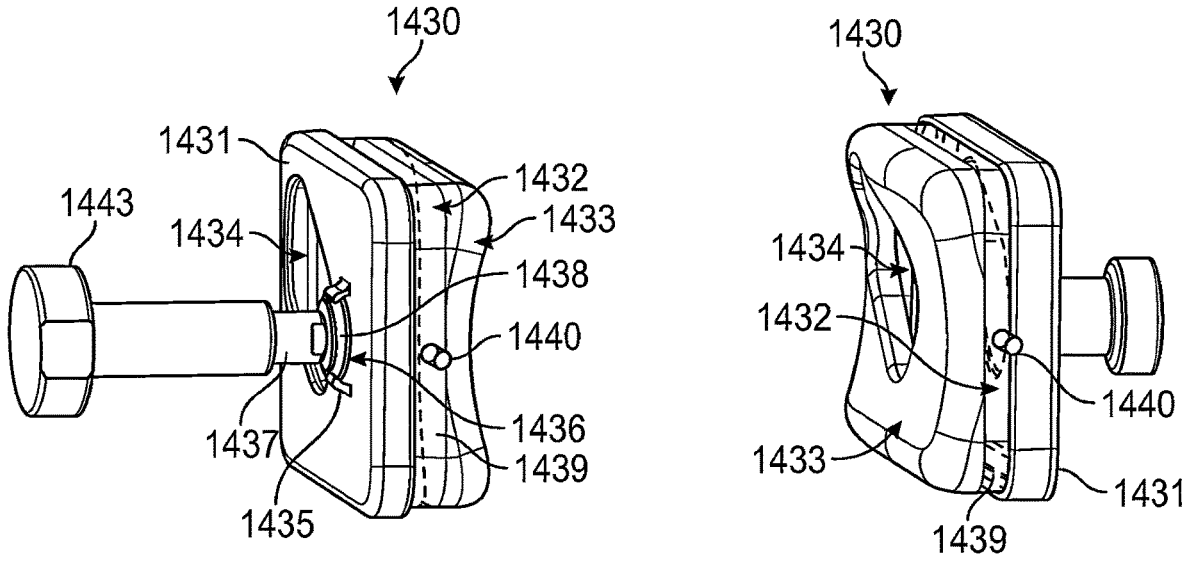
FIG. 9 depicts a perspective view of another exemplary central head support and another pair of stabilization assemblies usable with the HFD of FIG. 1.
Figure 9:
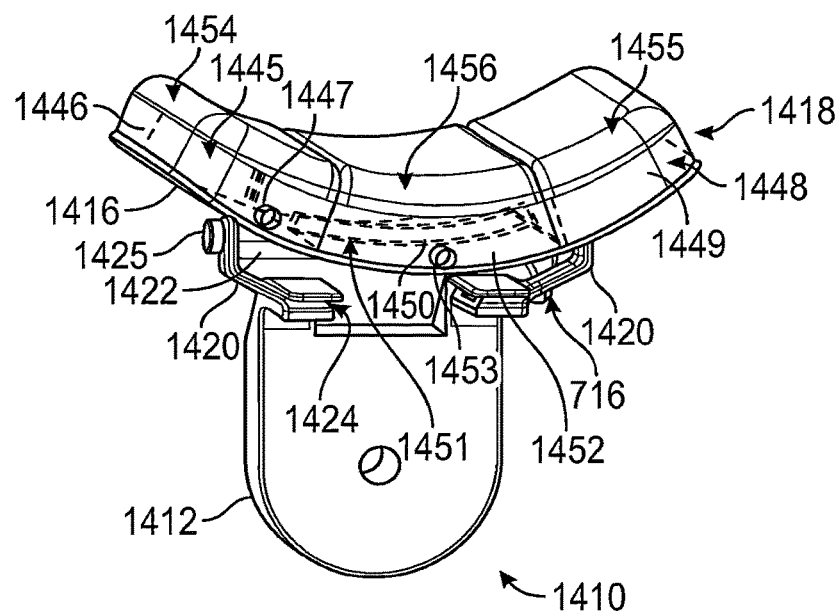

In some instances, a non-invasive HFD configuration may be desired where the stabilization assemblies have the form of pads instead of pins, where the pads provide the lateral stabilization. Additionally, the pads may be configured with certain contact pressure control features to help promote blood flow to certain tissue areas to avoid or reduce the risk of tissue injury or trauma. FIG. 9 depicts pads (1430) for the stabilization assemblies (816) to provide for a non-invasive stabilization with the HFD (600). FIG. 9 also depicts a central head support (1410) that can be used in place of the central head support (700) of the HFD (600). The central head support (1410) incorporates a pivoting cushion feature and features that aid in controlling contact pressure, similar to the central head support (1310) described above. The central head support (1410) differs from the central heads support (1310) in that a cushion (1418) replaces the cushion (1318). Similar to the cushion (1318) described above, the pads (1430) include features that aid in controlling pressure at the lateral stabilization contact areas where the pads (1430) contact the patient's head.

The central head support (1410) comprises a slot (1424) that receives the beam portion (910) of the connector (904) of the positioning assembly (900). The central head support (1410) further comprises a body (1412) and an attachment feature on the body (1412), where the attachment feature is in the form of a starburst configured to connect with an operating table or other structure directly or indirectly via one or more intermediate structures. For example, in some instances a base unit, such as those available from pro med instruments GmbH, attaches to an operating table and the attachment feature connects with the base unit. In some instances an adapter, such as a swivel adapter or other adapter available from pro med instruments GmbH, may connect with the base unit, and the attachment feature of the central head support (1410) connects with the adapter. In view of the teachings herein, various ways to connect the central head support (1410) with a stable structure such as an operating table, etc. will be apparent to those of ordinary skill in the art.

The central head support (1410) also comprises a base (1416) that connects with the body (1412) and that holds or retains the cushion (1418). The cushion (1418) may connect with the base (1416) by way of an adhesive, mechanical fasteners such as screws or hook and loop, or other ways that will be apparent to those of ordinary skill in the art. In some versions, the cushion (1418) is selectively connected with the base (1416) such that the cushion (1418) may be disposable or may be removed for cleaning and sterilization after use. The cushion (1418) is configured to contact the head of the patient when the HFD (600) is used to support and stabilize the patient. In the present example, the base (1416) connects with the body (1412) by way of a pair of arms (1420) that extend from the body (1412) outward and upward. The base (1416) comprises a connection member (1422) defining an axis extending transversely across the base (1416). The connection member (1422) comprises a pair of bores on each side and each bore aligns with a respective bore in each of the arms (1420). The axis defined by the connection member (1422) extends along the bores of the connection member (1422) such that the axis defines a pivoting axis about which the base (1416) and connected cushion (1418) are pivotable. A pair of fasteners (1425) extend through the bores of the arms (1420) and engage the bores of the connection member (1422) to pivotably connect the base (1416) with the body (1412) of the central head support (1410). The fasteners (1425) may be tightened to secure the position of the base (1416) and connected cushion (1418), and conversely the fasteners (1425) may be loosened to permit pivotable adjustment of the base (1416) and connected cushion (1418).

In use, the central head support (1410) is configured to provide subjacent support to the head of the patient. In this manner, the central head support (1410) defines a plane that extends subjacent to the head of the patient when the head of the patient is supported by the central head support. In the present example, the central head support (1410) is positioned such that the plane defined by the central head support (1410) may be adjusted based on the pivoting action of the base (1416) and connected cushion (1418). Therefore, the plane defined by the central head support (1410) is not limited to being parallel to a floor, or orthogonal to a direction of gravitational force on the central head support (1410).

The central head support (1410) is configured to adjust a spacing between the central head support (1410) and positioning assembly (900) in the same manner as discussed above with respect to the central head support (700) and the positioning assembly (900). For instance, the connector (904) adjustably connects with the body (1412) of the central head support (1410). As illustrated, within the body (1412) is a slot (1424). The slot (1424) receives the beam portion (910) of the connector (904). The profile of the beam portion (906) has a complementary shape to the slot (1424). In the present example the beam portion (906) and slot (1424) together form a dovetail interface. In this manner the connector (904) is translatable along the slot (1424), which adjusts the spacing between the positioning assembly (900) and the central head support (1410). To control the adjustability of the connector (904) within the slot (1424), the central head support (1410) comprises the actuator (716) and the lock feature (718), which are configured and operable in the same manner as described above. In this configuration, the connector (904) is adjustable along or parallel to the plane defined by the central head support (1410) to change a position of the positioning assembly (900) relative to the central head support (1410).

The pads (1430) comprise a housing (1431), a first chamber (1432), and a second chamber (1433). A bore or cut-out (1434) extends through the housing (1431), the first chamber (1432), and the second chamber (1433). The bore (1434) is located such that it is configured to receive a patient's ear during stabilization so as to protect the patient's ear from excessive compression and pressure, and instead direct such pressure and compressive force on the patient's skull. Located on the housing (1431) is also an annular flange (1435) that defines a slot (1436) configured to connect with the remainder of the stabilizing assembly (816). In the present example, the stabilizing assembly includes a collar (1437) having a flange (1438) that fits within the slot (1436). With this configuration, the pad (1430) can be adjusted about an axis defined by and extending through the bore (814) as illustrated above in FIG. 1.

The first chamber (1432) of the pad (1430) defines an internal space (1439) that is configured to be filled with a fluid, which may be a liquid or gas or combination. There is also a port (1440) that can be opened and closed that connects with the first chamber (1432) and provides access to the internal space (1439) of the first chamber (1432). In this manner, the fluid can be delivered to or vented or extracted from the internal space (1439) of the first chamber (1432) by way of the port (1440).

When the pads (1430) are used with each stabilizing assembly (816), in some versions the ports (1440) are connected by a tube, hose, or conduit (1441). The tube (1441) may be connected to a valve (1457) and further connected to a fluid reservoir (1459) as described further below. In this configuration, by connecting the first chambers (1432) of multiple pads (1430), the pressure within the first chambers (1432) is the same, and the pressure changes in the same fashion too as the first chambers (1432) may be filled with more fluid to increase the pressure, or fluid vented from the first chambers (1432) to decrease the pressure within.

The first chamber (1432) is located between the housing (1431) and the second chamber (1433). Of course in other versions, in view of the teachings herein, it will be apparent to those of ordinary skill in the art that the locations of the first chamber (1432) and the second chamber (1433) may be switched. The second chamber (1433) of the pad (1430) is configured to be filled with a shape-conforming material as described above with respect to cushion (1318). In the present example, the second chamber (1433) is positioned to be adjacent to and in contact with the head of the patient. In one version, the shape-conforming material within the second chamber (1433) is one of either a gel, a foam, a granule material or a combination of such materials. In view of the teachings herein, other shape-conforming materials usable with the second chambers (1433) of pads (1430) will be apparent to those of ordinary skill in the art.

Figure 10:
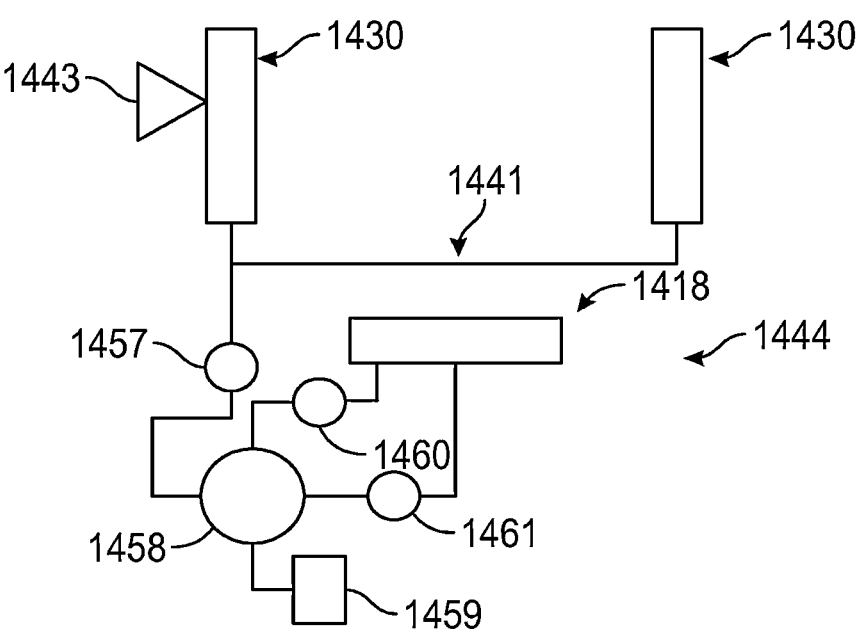
FIG. 10 depicts an exemplary fluid control system usable with the HFD of FIG. 1.

With the configuration of the pads (1430) described above, the pads (1430) are configured to provide a uniform distribution of contact pressure with the head of the patient when the head is supported by the stabilization assemblies (816) having the pads (1430). Moreover, the contact pressure can be increased by filling the first chamber (1432) with fluid via the port (1440) or via the tube (1441) connected with the ports (1440) as shown in FIG. 10, which depicts a fluid control system (1444). Conversely, the contact pressure can be decreased by venting the fluid from the first chamber (1432) as mentioned above. By reducing the contact pressure, blood flow can be restored to the area of the patient's head in contact with the pads (1430). In some instances, but not required in all versions, substantial venting of the fluid from the first chamber (1432) may cause the pads (1430) to deflate or reduce in size such that the pads (1430) no longer apply relevant pressure to the head of the patient. Similar to above, by reducing the contact pressure to the extent that the contact between the pads (1430) and the patient is lacking, blood flow can be restored to the area of the patient's head that was in contact with the pads (1430). By reducing contact pressure and providing for restoration of blood flow, tissue trauma or injury can be avoided or the risk reduced. Additionally, support of the patient's head can be maintained by the cushion (1418) of the central head support (1410) when reducing contact pressure between the pads (1430) and the patient's head so as to not sacrifice support of the patient when restoring blood flow to an area of tissue. In some instances, once sufficient time has elapsed to restore blood flow to the tissue area in contact with the pads (1430), the contact pressure can be increased again by filling the first chambers (1432) with the fluid to provide or restore an enhanced or a greater degree of stabilization.

In some versions of the HFD (600) configured with the pads (1430), both of the laterally positioned pads (1430) are connected via the tube (1441) and the pads (1430) are kept at the same pressure at all times within each of the pads (1430). In some other versions, it is not required to connect both the laterally positioned pads (1430) with the tube (1441), and thus each of the pads (1430) can be controlled independent from the other in terms of its pressure. Still yet, various valve placements may be incorporated with the tube (1441) such that the pads (1430), even if connected via the tube (1441), may be configured to be controlled independently. In view of the teachings herein, other ways to configure the pads (1430) and control the pressure within will be apparent to those of ordinary skill in the art. By way of example only, and not limitation, the pressure demands within the pads (1430) may differ with patient positions where the skull clamp (800) is rotated about the patient's head as described above.

In some versions of the HFD (600) configured with the pads (1430), the pressure the pads (1430) apply to the patient's head is adjustable using a torque screw (1443). The torque screw (1443) is a component of one of the stabilizing assemblies (816). Tightening the torque screw (1443) increases the pressure applied by the pads (1430) to the patient's head. In the illustrated version, the single torque screw (1443) is on one side, and the two pads (1430) are connected by the tube (1441) such actuation of the torque screw (1443) changes the pressure in both the pads (1430). In some other versions, multiple torque screws (1443) could be used, one associated with each of the pads (1430) such that the pads (1430) may not be connected by the tube (1441). In some versions, the initial stabilization may be accomplished using the torque screw (1443). After setting the torque screw (1443) initially, subsequent pressure adjustments could be made by adjusting the amount of fluid within the first chambers (1432) of the pads (1430), e.g. by directing more fluid to the first chambers (1432) to increase the pressure, or by venting fluid from the first chambers (1432) to decrease the pressure. In other words, in some versions, whether or not the torque screw (1443) is included, the contact pressure provided by each of the pads (1430) can be controlled or adjusted separate and independent from the torque screw (1443). In some versions, the torque screw (1443) can be omitted altogether, and replaced with a conventional skull pin assembly. In view of the teachings herein, other ways to use either the torque screw (1443), a fluid control system (1444) as shown in FIG. 10, or both in combination will be apparent to those of ordinary skill in the art.

As mentioned, the HFD (600) can be configured with the central head support (1410) having the cushion (1418). The cushion (1418) comprises a multi-chamber structure with a first chamber (1445) having an internal space (1446) that is configured to be filled with a fluid. The fluid may be a gas or a liquid. The first chamber (1445) includes a port (1447) that is configured to provide access to the internal space (1446). The fluid may be directed to the internal space (1446) within the first chamber (1445) or extracted from or vented from the internal space (1446) of the first chamber (1445). When venting fluid from the first chamber (1445), all or a portion of the fluid may be released or vented from the internal space (1446). The cushion further comprises a second chamber (1448) having an internal space (1449) that is configured to be filled with the fluid, or fluid may be extracted from or vented from the internal space (1449) of the second chamber (1448). When venting fluid from the second chamber (1448), all or a portion of the fluid may be released or vented from the internal space (1449). In the present example, the internal space (1446) of the first chamber (1445) and the internal space (1449) of the second chamber (1448) are in fluid communication by way of a connection tube (1450) that extends between the internal spaces (1446, 1449) of the first and second chambers (1445, 1448).

The cushion (1418) further comprises a third chamber (1451) positioned between the first and second chambers (1445, 1448). In this configuration, the first and second chambers (1445, 1448) collectively define a pair of outer chambers while the third chamber (1451) defines a middle chamber. The third chamber (1451) also comprises an internal space (1452), and the connection tube (1450) extends through the internal space (1452) of the third chamber (1451). The internal space (1452) of the third chamber is configured to be filled with the fluid similar to the first and second chambers (1445, 1448). The fluid may be added to or removed from the internal space (1452), which can change the pressure within this area of the cushion (1418). The third chamber (1451) comprises a port (1453) similar to the first chamber (1445). The port (1453) provides access to the internal space (1452) and is used to direct fluid to the internal space (1452) or vent fluid from the internal space (1452).

The cushion (1418) further comprises a fourth chamber (1454), a fifth chamber (1455), and a sixth chamber (1456), each configured be filled with a shape-conforming material. The first chamber (1445) is positioned subjacent to the fourth chamber (1454), and the fourth chamber (1454) is configured to contact the head of the patient. The second chamber (1448) is positioned subjacent to the fifth chamber (1455), and the fifth chamber (1455) is configured to contact the head of the patient. The third chamber (1451) is positioned subjacent to the sixth chamber (1456), and the sixth chamber (1456) is configured to contact the head of the patient. In view of the teachings herein, it will be apparent to those of ordinary skill in the art that the relative positions of the first and fourth chambers (1445, 1454), the second and fifth chambers (1448, 1455), and the third and sixth chambers (1451, 1456) may be switched in other versions. In one version, the shape-conforming material within the fourth, fifth, and sixth chambers (1454, 1455, 1456) is one of either a gel, a foam, a granule material or a combination. In view of the teachings herein, other shape-conforming materials usable with the cushion (1418) will be apparent to those of ordinary skill in the art.

With the configuration of the cushion (1418) described above, the cushion (1418) is configured to provide a various pressure profiles depending on the manner of adjustments with the fluid and each of the respective internal spaces (1446, 1449, 1452). For instance, in some versions, a uniform distribution of contact pressure can be achieved where the third chamber (1451) is configured to hold the same amount of fluid per unit of volume within the internal space (1452) as in the internal spaces (1446, 1449) of the first and second chambers (1445, 1448). Still in other versions, the outer chambers may have matching pressures while the middle chamber has a pressure that may be higher or lower than the pressure within the outer chambers. Furthermore, in this configuration with differing pressures between the outer chambers and the middle chamber, the fluid may be vented and/or added in a controlled fashion to provide a way to promote blood flow to an area of the patient's tissue in contact with a portion of the cushion (1418) while maintaining secure stabilization of the patient's head.

By way of example only, and not limitation, in one version, a patient is initially stabilized with the pads (1430) applying the same contact pressure to the lateral portions of the patient's head. In the initial stabilization, the cushion (1418) is configured such that the outer chambers and middle chamber also apply the same contact pressure to the back portion of the patient's head. In this example the HFD (600) is used with the patient in a supine position, but this is not necessary in all examples such that the HFD (600) may be used with the patient in other positions. After some time has passed, the pressure within the pads (1430) and/or the cushion (1418) can be manipulated so that blood flow can be restored or increased to the areas where the tissue of the patient's head contacts portions of the HFD (600). Moreover, this manipulation of pressure comprises a short term relief or reduction of pressure to promote increased blood flow to the tissue, followed by an increase in pressure after a period of time has passed to provide for enhanced stabilization. Furthermore, this manipulation of pressure can be performed in an alternating fashion among the pads (1430) and/or chambers of the cushion (1418). By using this alternating fashion, the tissue areas in contact with the HFD (600) are treated with restored or increased blood flow while maintaining an acceptable degree of stabilization.

An example of the alternating pressure relief and restoration sequence can include as a first step, after an initial stabilization is configured, reducing the pressure in the pads (1430) to give an amount of time to restore blood flow to the lateral portions of the patient's head. Note that in some such examples the pressure in the pads (1430) may not be reduced at all, and the pressure relief sequence may be limited to the multi-chamber cushion (1418). Note also that in other examples, the first step may be to perform a pressure relief step or process on the multi-chamber cushion (1418) and thereafter perform a pressure relief step on one or both of the pads (1430). In the present example, however, after the pressure in the pads (1430) has been reduced and some time has passed where blood flow has been increased to the tissue areas of the patient in contact with the pads (1430), the pressure in the pads (1430) is then restored to its initial level.

Thereafter, the middle chamber defined by the third chamber (1451) is vented to reduce its pressure. This action reduces the force or pressure applied to the patient's head at the middle chamber and thus allows for increased blood flow to this back area of the patient's head in contact with the middle chamber. In this case, the outer chambers, defined collectively by the first and second chambers (1445, 1448), remain at their original or initial pressure, or experience a higher pressure. Thus the outer chambers and the pads (1430) provide stabilization to the patient's head while the tissue area in contact with the middle chamber is receiving a period of increased or restored blood flow to prevent or reduce the risk of tissue trauma in this area.

For the sake of further clarity, the middle chamber of the cushion (1418) comprises both the third chamber (1451) that is configured to contain the fluid, as well as the sixth chamber (1456) that is configured with the shape-conforming material. Similarly, with the pair of outer chambers, one of the outer chambers comprises the first chamber (1445) that is configured to contain the fluid, as well as the fourth chamber (1454) that is configured with the shape-conforming material. And the other of the outer chambers comprises the second chamber (1448) that is configured to contain the fluid, as well as the fifth chamber (1455) that is configured with the shape-conforming material. As will be understood in view of the teachings herein, the pressure relief discussed above within the outer chambers and the middle chamber occurs by changing the fluid volume within the respective internal spaces (1446, 1449, 1452) of the first, second, and third chambers (1445, 1448, 1451), while the increase in blood flow based on the pressure relief occurs at the tissue areas in contact with the respective fourth, fifth, and sixth chambers (1454, 1455, 1456) having the shape-conforming material. In other configurations, the fluid-filled chambers may be the chambers in contact with the patient's head while the shape-conforming containing chambers may be located beneath or subjacent to the respective fluid-filled chambers. In view of the teachings herein, other configurations for the chambers will be apparent to those of ordinary skill in the art.

Returning again to the example above of a pressure relief sequence, after the pressure in middle chamber of the cushion (1418) has been reduced and some time has passed where blood flow has been increased to the tissue area of the patient in contact with the middle chamber, and specifically the sixth chamber (1456), the pressure in the middle chamber of the cushion (1418) is then restored to its initial level. Thereafter, the pair of outer chambers are vented to reduce their pressure by venting or extracting fluid from the respective first and second chambers (1445, 1448). This action reduces the force or pressure applied to the patient's head at the outer chambers, and thus allows for increased blood flow to these areas of the patient's head in contact with the outer chambers, and more specifically at the areas of contact with the respective fourth and fifth chambers (1454, 1455). In this case, the middle chamber experiences a higher pressure, while the pads (1430) remain at their original or initial pressure. Thus the middle chamber and the pads (1430) provide stabilization to the patient's head while the tissue area in contact with the outer chambers is receiving a period of increased or restored blood flow to prevent or reduce the risk of tissue trauma in this area.

After the pressure in outer chambers of the cushion (1418) has been reduced and some time has passed where blood flow has been increased to the tissue area of the patient in contact with the outer chambers, and specifically the fourth and fifth chambers (1454, 1455), the pressure in the outer chambers of the cushion (1418) is then restored to its initial level. The above described pressure relief process can be conducted multiple times as needed or desired to help reduce the risk of tissue injury or trauma. Moreover, these pressure relief actions can be completed in any order as the circumstances require or dictate such that the example order described above should not be considered a required order or the only order or sequence.

With the HFD (600) configured with the pads (1430) and the central head support (1410) as described above, the fluid connection between the first chambers (1432) of the pads (1430) via the tube (1441) allows for the pressure in each of the pads (1430) to be the same and to be simultaneously adjusted such that while the pressure in the pads (1430) changes, it does so in the same manner and to the same degree. With the pads (1430) generally located on opposite sides of the patient's head, the fluid connection between the first chambers (1432) of the pads (1430) allows for pressure changes within the pads (1430) to promote blood flow to the tissue areas contacted by the pads (1430) without altering the differential in the force that is applied to the opposing sides of the patient's head by the respective pads (1430). This configuration allows for the pressure changes within the pads (1430) without causing the patient's head to move or change position.

For instance, in one example, the initial force applied to each side of the patient's head by each of the pads (1430) may be 20 newtons, and thus the differential in force would be zero because the force applied by each of the pads (1430) is the same. When an example pressure relief process has been performed, the force applied to each side of the patient's head by each of the pads (1430) may now be 50 newtons, and thus the differential in force maintained at zero because the force applied by each of the pads (1430) remains the same. Again, while in the present example the pads (1430) may be fluidly connected by the tube (1441), this is not required in all versions. For instance, in some other versions the pads (1430) may be independently adjustable or controllable regarding their pressure based on fluid volumes within the first chambers (1432).

Similar to the pads (1430), the fluid connection between the first chamber (1445) and the second chamber (1448) of the cushion (1418) via the connection tube (1450) allows for the pressure in each of the outer chambers of the cushion (1418) to be the same and to be simultaneously adjusted such that while the pressure in the outer chambers of the cushion (1418) changes, it does so in the same manner and to the same degree. As shown and described, the outer chambers of the cushion (1418) are generally located on opposite sides of the sagittal plane of the patient's head when in the supine position such that the outer chambers of the cushion (1418) are symmetrically located about the sagittal plane dividing the patient's head into left and right portions. The fluid connection between the outer chambers of the cushion (1418) allows for pressure changes within the outer chambers of the cushion (1418) to promote blood flow to the tissue areas contacted by the outer chambers of the cushion (1418) without altering the differential in the force that is applied to the patient's head by the respective outer chambers of the cushion (1418). This configuration allows for the pressure changes within the outer chambers of the cushion (1418) without causing the patient's head to move or change position, i.e. rotating about the patient's longitudinal axis because of an uneven force applied by one of the outer chambers of the cushion (1418) compared to the other outer chamber of the cushion (1418).

IV. Exemplary Fluid Control Systems and Methods

FIG. 10 depicts the fluid control system (1444) usable with the HFD (600) configured with the pads (1430) and the cushion (1418) as shown schematically. As described above in detail, the pads (1430) provide the lateral stabilization to the patient's head, and the cushion (1418) provides subjacent support and stabilization. The torque screw (1443) connects with one of the pads (1430) to permit increasing or decreasing the pressure the pad (1430) applies to the patient's head. The connection tube (1441) connects the pads (1430) together such that they are in fluid communication. As described above, the connection tube (1441) connects the first chambers (1432) of the respective pads (1430). In this configuration, the pressure in each of the pads (1430) is the same and each of the pads (1430) imparts the same force on the patient's head.

Also connected with the connection tube (1441) is a valve (1457). The valve (1457) is configured to selectively vent fluid from the pads (1430) to reduce the pressure within the pads (1430) or to permit additional fluid to flow to the pads (1430) to increase the pressure within the pads (1430). The valve (1457) connects with a pump (1458), which is configured to supply additional fluid to the pads (1430) when desired. In some versions, the pump (1458) can also be configured to direct vented or extracted fluid away from the pads (1430). In fluid communication with the pump (1458) is a fluid reservoir (1459). The fluid reservoir (1459) is configured to provide additional fluid to be delivered via the pump (1458) to the pads (1430). In some instances, venting fluid from the pads (1430) involves opening the valve (1457) and operating the pump (1458) to move fluid from the pads (1430) to the fluid reservoir (1459). The pump (1458) can also be used without the fluid reservoir (1459) such that the fluid reservoir (1459) may be omitted in some versions. In such versions, the pump (1458) may be configured to deliver air from the surrounding environment to the pads (1430). Similarly, venting fluid from the pads (1430) in such versions may involve venting air from the pads (1430) back to the surrounding environment instead of venting to the fluid reservoir (1459). In some examples, the fluid reservoir (1459) itself can be considered the surrounding environment.

Figure 12:
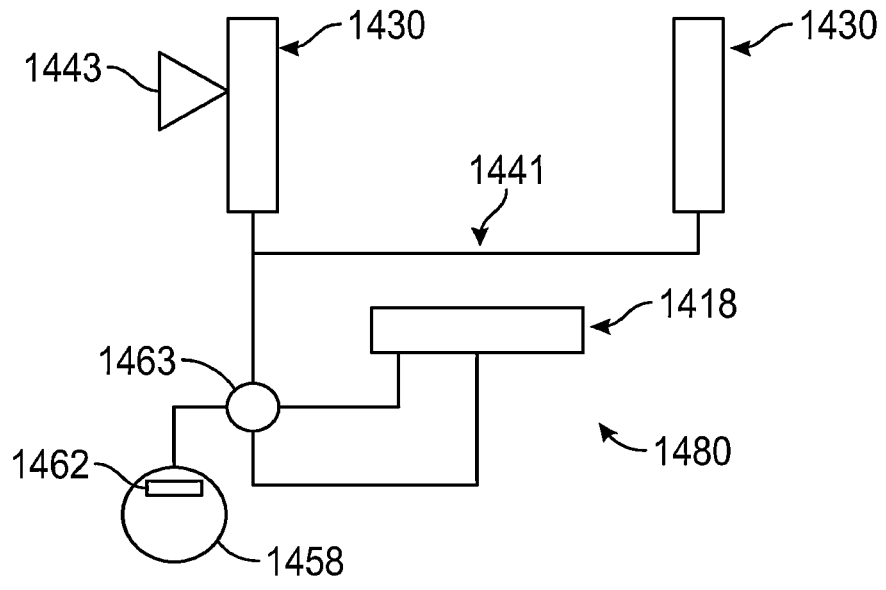
FIG. 12 depicts another exemplary fluid control system usable with the HFD of FIG. 1.

In one version having a simplified configuration for the fluid control system (1444), the fluid reservoir (1459) is omitted, and the pump (1458) comprises a hand pump or foot pump having a pressure gauge and configured to be manually operated. In this example, the pump (1458) is selectively connectable with the various valves (1457, 1460, 1461) to adjust fluid volumes and pressure within the pads (1430) and cushion (1418). In some versions, such as illustrated in FIG. 12, a fluid control system (1480) can have a single valve (1463) that is switchable can be used instead of the multiple valves (1457, 1460, 1461). In such an instance, the valve (1463) connects with the pump (1458) as well as the respective ports (1447, 1453) of the cushion (1418). As also shown, the valve (1463) can also be connected with the pads (1430) via the connection tube (1441), although this additional fluid connection is not required in all versions and may be controlled by a separate fluid control system. When controlling fluid within the fluid control system (1480), the valve (1463) is configured such that fluid can be directed to any of the fluid holding chambers of the cushion (1418) and/or the pads (1430). Moreover, the valve (1463) can be configured to direct fluid to more than one of the chambers of the cushion (1418) and/or pads (1430) at the same time. The pump (1458) is configured with a pressure gauge (1462) and the pressure gauge (1462) is configured to indicate a pressure within the chambers to which the valve (1463) is actively in fluid communication with. In view of the teachings herein, other configurations for the various fluid control systems will be apparent to those of ordinary skill in the art. For instance, it will be appreciated that to direct the fluid, a single or multiple pumps may be used, a single or multiple valves may be used, and a variety of ports and connection tubes may be used.

In the present example, the pump (1458) also connects two other valves (1460, 1461) that connect with the respective ports (1447, 1453) of the cushion (1418). The valves (1460, 1461) are configured similar to the valve (1457) and thus the pump (1458) can also be operated to provide additional fluid from the fluid reservoir (1459) to either or both of the outer chambers and middle chamber of the pad (1418). As described above, the fluid is provided to the first and third chambers (1445, 1451) of the cushion (1418). Furthermore, in this configuration, fluid can be vented or extracted from the cushion (1418) by either venting the fluid to the atmosphere via the valves (1460, 1461) in one example, or by opening the valves (1460, 1461) and operating the pump (1458) to transfer fluid to the fluid reservoir (1459). In view of the teachings herein, other ways to configure and operate the fluid control system (1444) to manipulate the pressures within the pads (1430) and cushion (1418) will be apparent to those of ordinary skill in the art.

Figure 11:
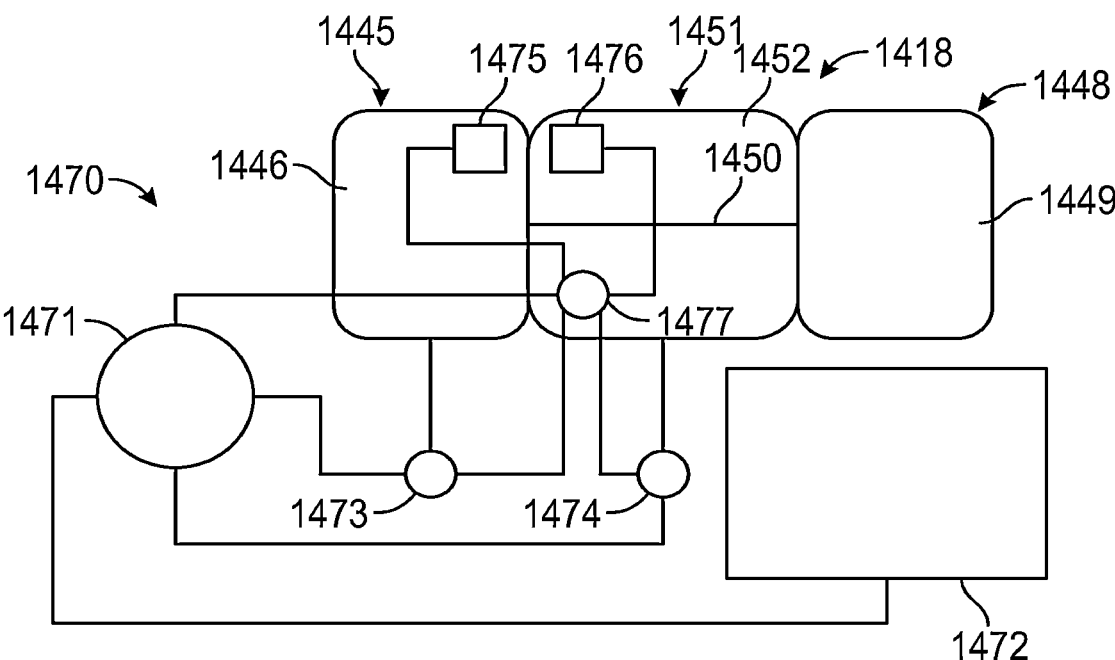
FIG. 11 depicts another exemplary fluid control system usable with the HFD of FIG. 1.

FIG. 11 shows another exemplary fluid control system (1470) that is usable with the HFD (600) when configured with the multi-chamber cushion (1418). The fluid control system (1470) is configured to provide fluid control where the outer chambers and middle chamber can be vented and refilled in an alternating manner as described above. Again, as discussed above this alternating venting or pressure relief provides for the ability to increase blood flow to certain areas of the patient's head, while also maintaining adequate stabilization of the patient's head.

As shown in the illustrated version of FIG. 11, the fluid control system (1470) comprises a pump (1471) connected to a fluid reservoir (1472) containing fluid. With the fluid control system (1470) the pump (1471) further connects with two valves (1473, 1474). One of the valves (1473) connects with the port (1447) of the first chamber (1445) of the cushion (1418), and the other valve (1474) connects with the port (1453) of the third chamber (1448) of the cushion (1418). The connections between the pump (1471), the fluid reservoir (1472), the valves (1473, 1474), and the ports (1447, 1453) are such that these components are in fluid communication so that fluid can be transported between these components. Accordingly, the fluid control system (1470) is configured to either direct fluid to the cushion (1418) or extract or vent fluid from the cushion (1418). As described above, the first chamber (1445) of the cushion (1418) connects with the second chamber (1448) by way of tube (1450) such that fluid changes impact both chambers (1445, 1448) in the same manner and to the same degree such that the pair of outer chambers have the same pressure.

Within the internal space (1446) of the first chamber (1445), the fluid control system (1470) includes a pressure sensor (1475). In some other versions, the pressure sensor (1475) can be instead located within the internal space (1449) of the second chamber (1448). The fluid control system (1470) further includes a pressure sensor (1476) located within the internal space (1452) of the third chamber (1451). In the present example, the pressure sensors (1475, 1476) connect with a control unit (1477). In the illustrated example, the control unit (1477) is also located within the internal space (1452) of the third chamber (1451). In some other versions, the control unit (1477) can be located in other positions within or outside of the cushion (1418). Also connected with the control unit (1477) are the valves (1473, 1474) and the pump (1471). The connections between the control unit (1477), the pump (1471), the valves (1473, 1474), and the sensors (1475, 1476) are such that these components are in electrical communication so that electrical signals can be transmitted and/or received by between these components. The components described here that transmit and/or receive signals are powered by batteries contained within these components. Of course in other versions, separate power sources may be used instead of or in addition to the batteries within the components. In view of the teachings herein, other ways to provide power to the components described here will be apparent to those of ordinary skill in the art.

With the configuration described above for FIG. 11, in operation the fluid control system (1470) can be configured such that the control unit (1477) is operable to change the fluid volumes within the first, second, and third chambers (1445, 1448, 1451) using signals from the pressure sensors (1475, 1476). For example, after some time has passed where a patient's head has been stabilized, it may be desired to selectively relieve pressure on the patient's head to restore blood flow to certain tissue areas contacted by the HFD (600) to reduce the risk of tissue trauma or injury as described above. With the fluid control system (1470), the control unit (1477) can be programmed to execute a set of instructions whereby the pair of outer chambers of the cushion (1418) and the middle chamber are manipulated in an alternating fashion to relieve pressure by venting or extracting the fluid to allow for a period of increased blood flow to the tissue before increasing the pressure by delivering fluid back to the respective chamber from which the fluid was previously vented or extracted.

By way of example only, and not limitation, one alternating sequence of pressure relief using the fluid control system (1470) may be conducted by initiating at the control unit (1477) a first pressure relief action or process where the fluid is vented or extracted from the first and second chambers (1445, 1448) until the pressure sensor (1475) reaches a predetermined value. The predetermined value may be a percentage reduction in the pressure sensor (1475) reading, or it may be a selected pressure value that may be determined to increase blood flow to the tissue area without compromising the stability of the patient. Once the pressure sensor (1475) reaches the predetermined value, a predetermined wait time ensues where time is provided for restoration or increase of blood flow to the areas of tissue in contact with the outer chambers. After a the predetermined wait time has elapsed, the control unit (1477) sends a signal to the pump (1471) and the valve (1473) to direct fluid to the first and second chambers (1445, 1448) to add fluid until the sensor (1475) reaches a predetermined value for pressure. This predetermined value may be the same as the pressure in the outer chambers of the cushion (1418) before the pressure relief cycle began, or it may be a different pressure value.

With the outer chambers refilled and having sufficient pressure to provide sufficient stabilizing force to the patient's head, next the control unit (1477) initiates a second pressure relief action or process where the fluid is vented or extracted from the third chamber (1451) until the pressure sensor (1476) reaches a predetermined value. The predetermined value may be a percentage reduction in the pressure sensor (1476) reading, or it may be a selected pressure value that may be determined to increase blood flow to the tissue area without compromising the stability of the patient. Once the pressure sensor (1476) reaches the predetermined value, a predetermined wait time ensues where time is provided for restoration or increase of blood flow to the areas of tissue in contact with the middle chamber. After a the predetermined wait time has elapsed, the control unit (1477) sends a signal to the pump (1471) and the valve (1474) to direct fluid to the third chambers (1451) to add fluid until the sensor (1476) reaches a predetermined value for pressure. This predetermined value may be the same as the pressure in the middle chamber of the cushion (1418) before the pressure relief cycle began, or it may be a different pressure value. From this point, once alternating cycle would have been completed and subsequent alternating cycles could continue immediately thereafter or after some time has passed.

In view of the teachings herein, other ways to configure and operate the fluid control system (1470) will be apparent to those of ordinary skill in the art. For instance, in some versions, the sensors (1475, 1476), the valves (1473, 1474), the pump (1471), and/or the control unit (1477) may be connected with an output display where the pressure and fluid data within the cushion (1418) may be visually displayed. In other instances, this data could be wirelessly transmitted to a device with a display, e.g. the fluid control system (1470) could be operable via an application installed on a computer or tablet. Still yet, in other versions, the control unit (1477) may be located outside the cushion (1418) and further connected with the pads (1430) using similar sensors and valves such that the control unit (1477) is able to control fluid deliver and extraction from both the chambers of the cushion (1418) as well as one or more of the pads (1430). Still further, in some versions the pump (1471) includes an integrated measurement of the pressure, such that one or both of the sensors (1475, 1476) may be effectively part of or within the pump (1471).

V. Exemplary Non-Invasive Head Fixation Device with Slidable Pads

Figure 13:
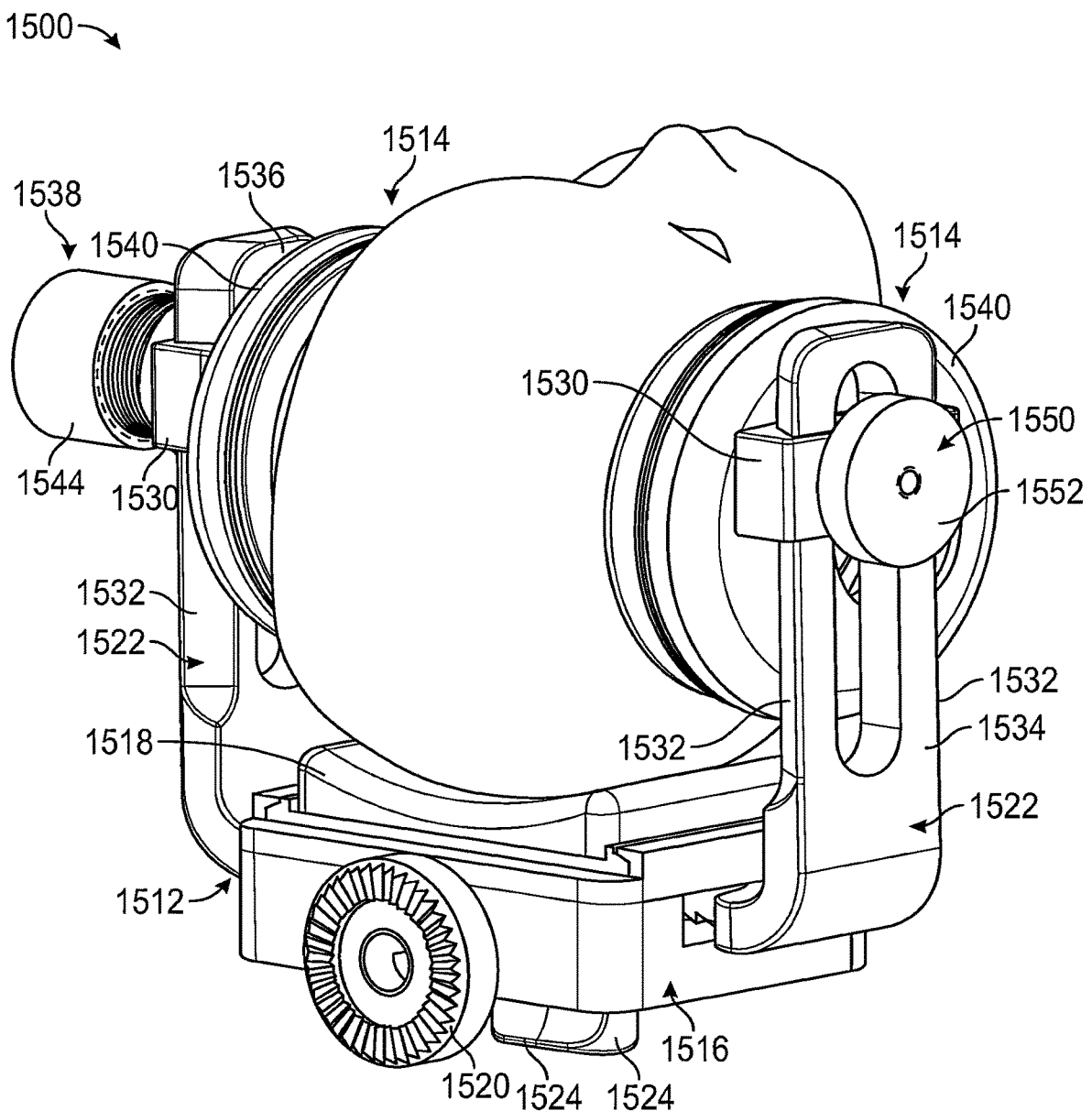
FIG. 13 depicts a perspective view of another exemplary HFD configured as a non-invasive HFD.
Figure 14:
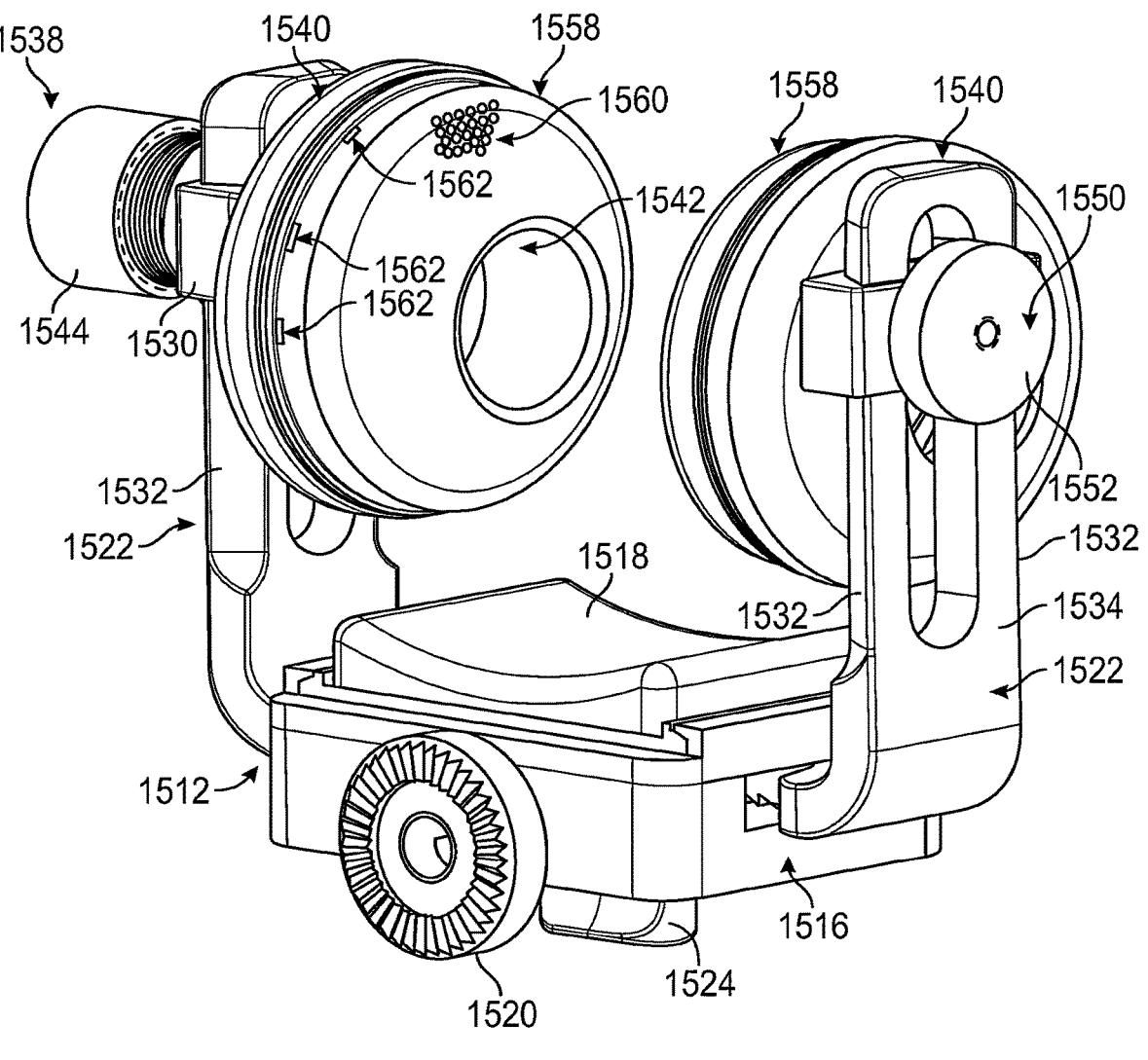
FIG. 14 depicts another perspective view of the HFD of FIG. 13.
Figure 15:
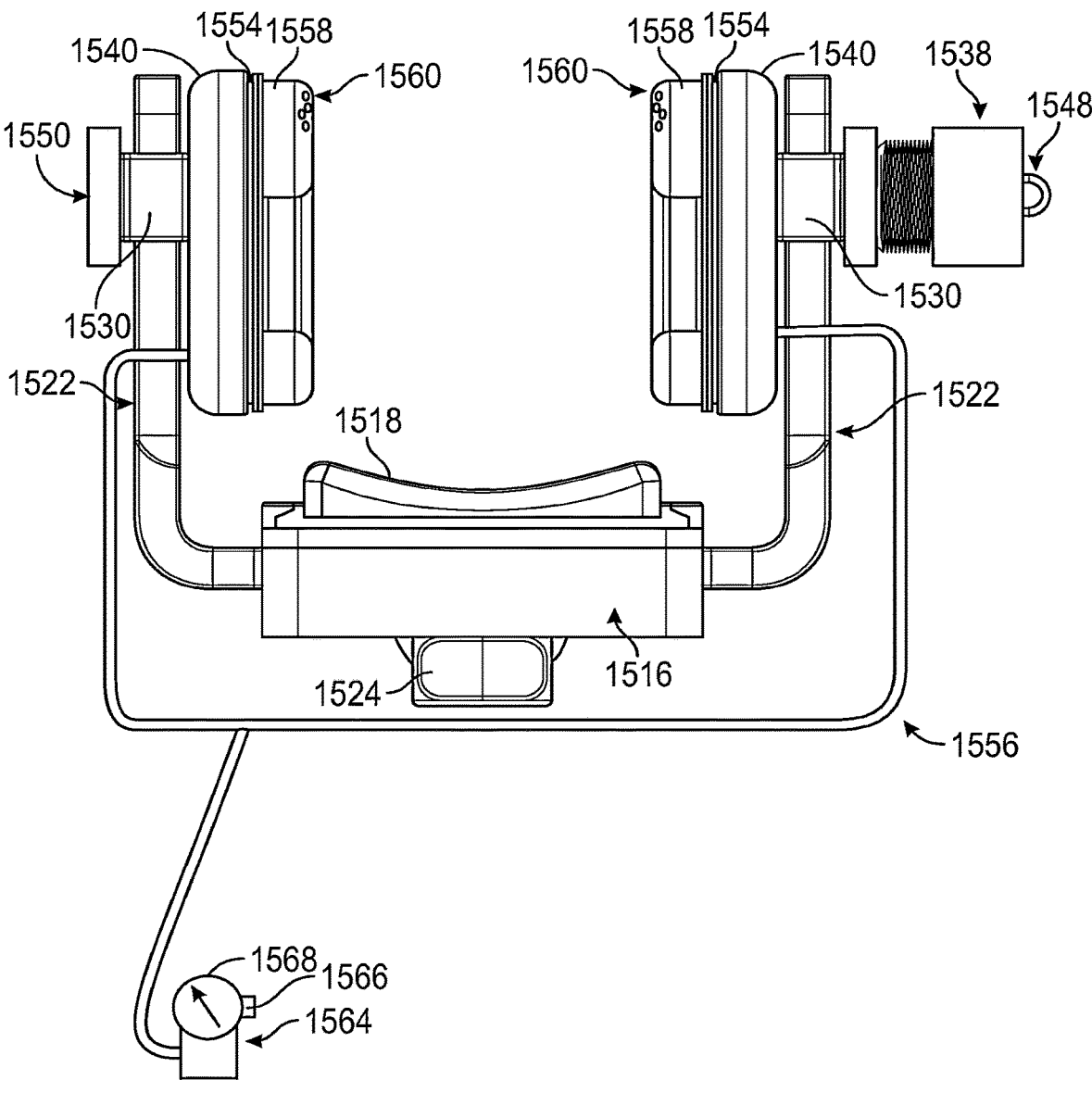
FIG. 15 depicts a front view of the HFD of FIG. 13, shown assembled with a pump.
Figure 16:
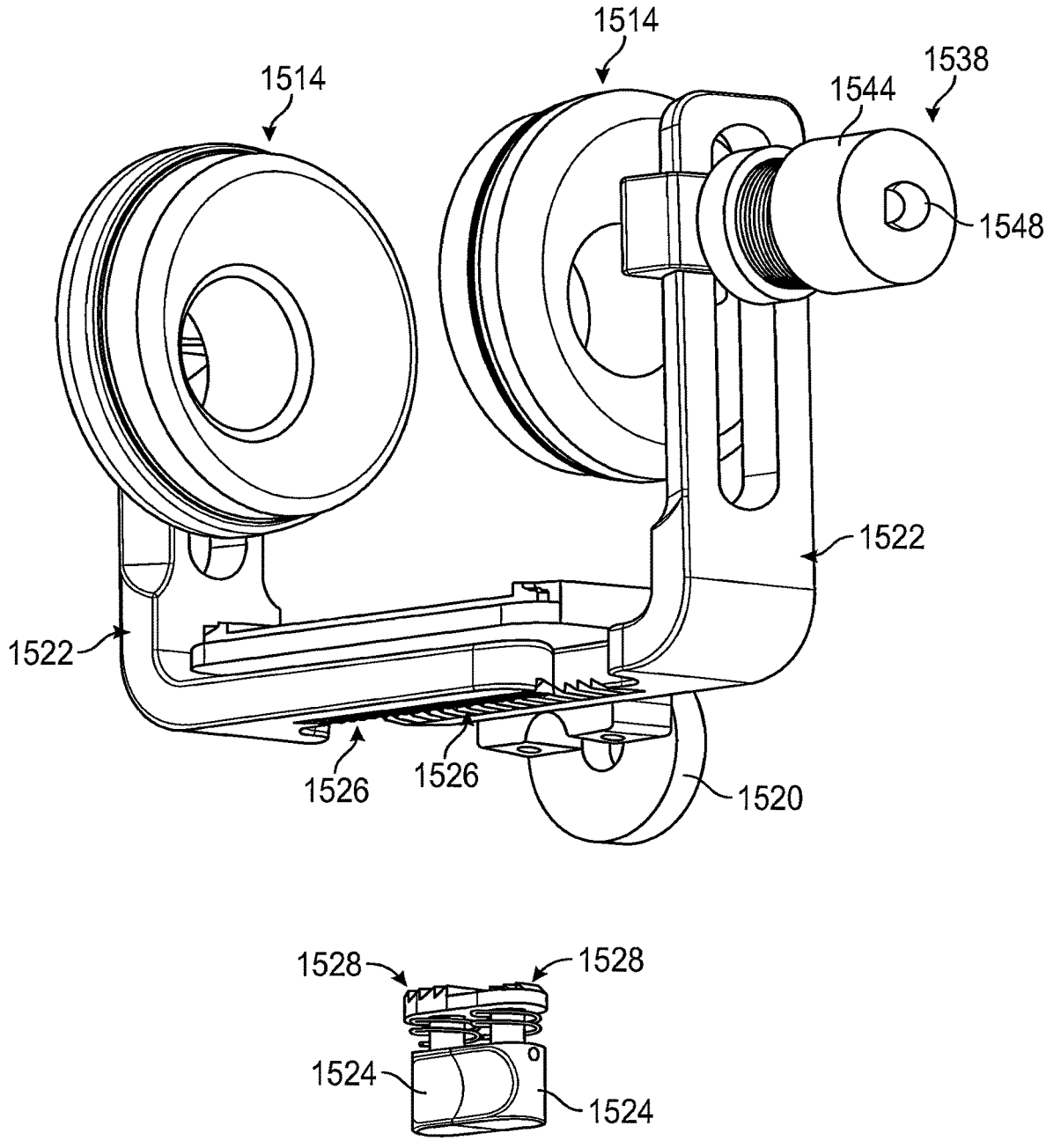
FIG. 16 depicts a partial exploded perspective view of the HFD of FIG. 13.
Figures 17, 18, 19:
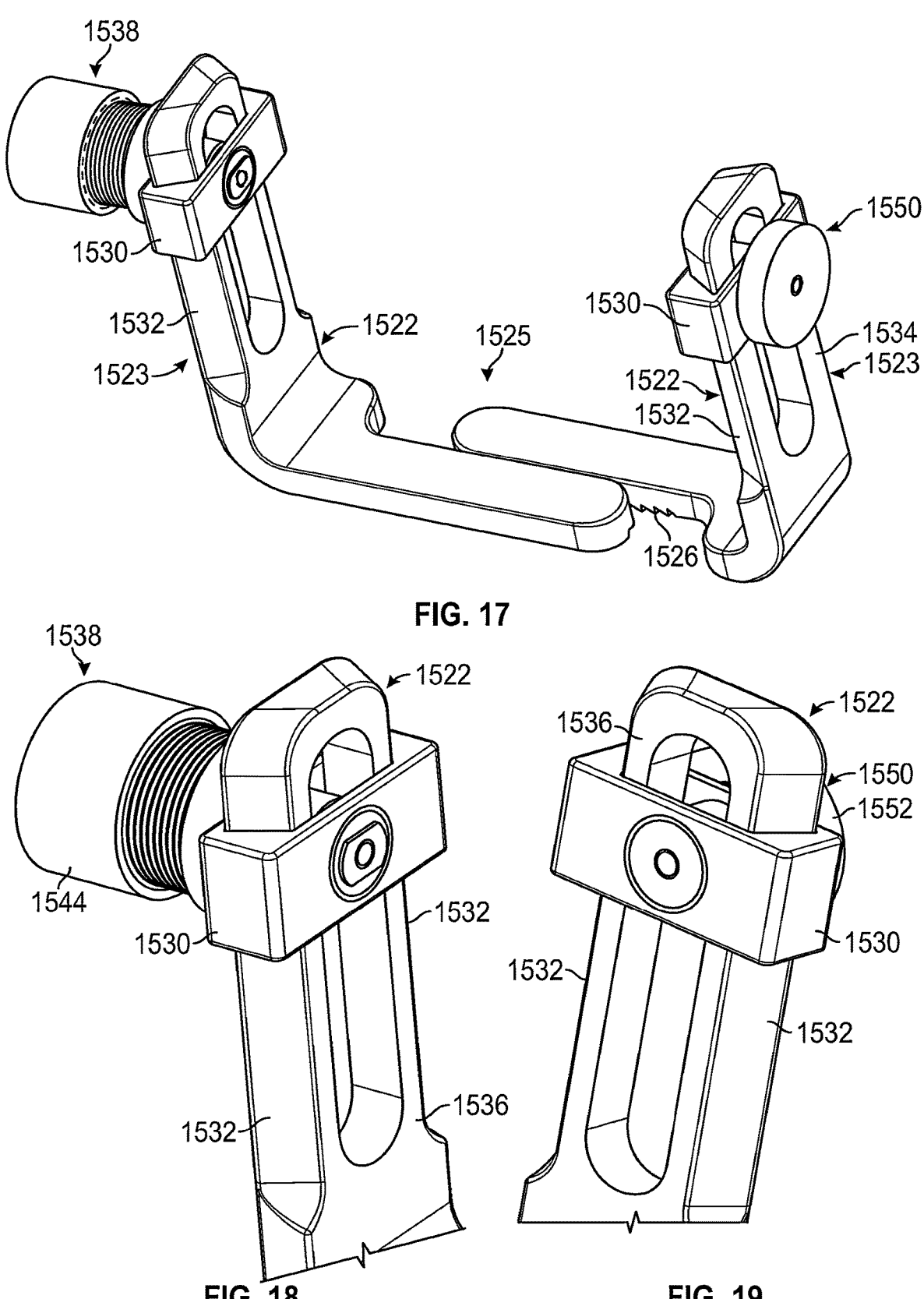
FIG. 17 depicts a partial perspective view of the HFD of FIG. 13, shown without a base assembly.
FIG. 18 depicts a partial perspective view an extension bar of the HFD of FIG. 13 with a torque screw.
FIG. 19 depicts a partial perspective view of another extension bar of the HFD of FIG. 13 with a locking bolt.

Referring to FIG. 13, an exemplary HFD (1500) is shown that is configured for non-invasive head stabilization, similar to the HFD (600), but that incorporates pads (1514) that are slidable relative to a support assembly (1512). Support assembly (1512) comprises a base assembly (1516) with an interchangeable and adjustable head cushion (1518). A gear ring or starburst connector (1520) at the base assembly (1516) connects the support assembly (1512) via a swivel adapter (not shown) with a base unit (not shown). In some instances, the support assembly (1512) is radiolucent as well as the swivel adapter and base unit. By way of example only, and not limitation, some exemplary swivel adapters and base units suitable for use with the support assembly (1512) are available from pro med instruments GmbH of Freiburg, Germany. The support assembly (1512) comprise two extension bars (1522), which can be positioned independently. At the bottom side of the base assembly (1516), two release knobs (1524) are located, each for one extension bar (1522). Pulling the knobs (1524) releases a ratchet mechanism inside the base assembly (1516) and the extension bars (1522) can be removed or rather adjusted. The adjustment of the extension bars (1522) allows for the extension bars (1522) to move laterally relative to base assembly (1516) so as to move toward or away from the head of a patient supported by the base assembly (1516) and head cushion (1518). In the present example, both extension bars (1522) have a separate ratcheting mechanism, which can be released separately or at the same time one-handed. In this way, one side's extension bar (1522) can be adjusted laterally independent of the other side's extension bar (1522). Still yet, actuating the release knobs (1524) at the same time allows for controlling the adjustment of each extension bar (1522) at the same time.

The two extension bars (1522) each comprise an L-shape with a lateral extending portion (1525) and an upright extending portion (1523). A toothed region extends (1526) along the lateral portion (1525). The toothed region (1526) is part of the ratchet mechanism and interlocks the extension bars (1522) relative to the base assembly (1516) by engaging with a complementary toothed feature (1528) of the release knobs (1524). Together, the toothed region (1526) of the extension bars (1522) and the toothed feature (1528) of the release knobs (1524) make up the ratchet mechanism.

Along the upright extending portion (1523) of each extension bar (1522), a slide (1530) is mounted and adjustable along the upright extending portion. The slides (1530) are fixed by connection with and tightening with a locking feature such as a bolt, torque screw, or other similar feature. Fixing the slides (1530) relative to the upright extending portions of the extension bars (1522) is achieved by the tightening deforming the slides (1530) elastically and pulling the slides (1530) in against the respective extension bar (1522). This adjustability of the slides (1530) along the upright extending portion of the extension bars (1522) allows a height adjustment of the pads (1514) connected with the slides (1530) as discussed further below. In the present examples, the cross-sectional shape of the upright extending portion (1523) of the extension bars (1522) is trapezoidal. Accordingly, the upright extending portion of the extension bars (1522) comprise sides (1532) that angle inward such that an outer surface (1534) of the extension bars (1522) has a greater width than an inner surface (1536). In the present example, this shape of the upright extending portion of the extension bars (1522) allows for the attachment of accessories like e.g. retractors, etc. by clamping such accessories onto the upright extending portion of the extension bars (1522).

In the present version of the HFD (1500), a torque screw (1538) connects with the slide (1530) on one side. At the inner side of the torque screw (1538) an interchangeable shell (1540) is mounted as a receptacle for the pad (1514). This shell (1540) is rotatable such that the pad (1514) can be adjusted. For instance the pad (1514) comprise an ear section (1542) in the present example and rotating the pad (1514) allows the ear section (1542) to be positioned to accommodate the patient's ears. In some instances the ear section (1542) may be referred to as an ear recess, indentation, or cut-out.

The torque screw (1538) also comprises an outer rotatable handle (1544). Turing the handle (1544) of the torque screw (1538) moves the shell (1540) and connected pad (1514) towards the head of the patient. Depending on the pressure inside the pad's (1514) air-chamber, as will be described below, a spring (1546) inside the torque screw (1538) is deformed and a scale (1548) at the outer side is uncovered, displaying the applied force.

In the present version of the HFD (1500), a locking bolt (1550) connects with the slide (1530) on the other side of the support assembly (1512) opposite to the side with the torque screw (1538). At the inner side of the bolt (1550) an interchangeable shell (1540) is mounted as a receptacle for the pad (1514). This shell (1540) is rotatable such that the pad (1514) can be adjusted. For instance the pad (1514) comprise an ear section (1542) in the present example and rotating the pad (1514) allows the ear section (1542) to be positioned to accommodate the patient's ears. In some instances the ear section (1542) may be referred to as an ear recess, indentation, or cut-out. The locking bolt (1550) also comprises an outer rotatable handle (1552). Depending on the direction of rotation, turning the handle (1552) of the locking bolt (1550) selectively fixes the slide (1530) relative to the upright extending portion (1523).

With the two extension bar (1522) configuration with the torque screw (1538) and locking bolt (5150) on each respective bar (1522), and the ability to adjust the pad (1514) position relative to the head of a patient (and also relative to a central axis (A1) of the support assembly (1512) that extends longitudinally through the base assembly (1516)), the pads (1514) can be positioned with an equal distance to the head resting onto the head cushion (1518). This leaves the head in a centered position on the main head cushion (1518). As will be described in greater detail below, the pads (1514) on each side comprise fluid chambers (1554) that are interconnected via a conduit or hose (1556), so the pressure onto the head from both sides is equal. This configuration further promotes maintaining the head in a centered position on the main head cushion (1518).

This centering promotion described above is lacking in certain other support and fixation structures where force is applied to the head from only, or from substantially, one side. For instance, some support and fixation structures are fixed at one side and then apply a pad or pin from the other side using an adjustable tightening and/or force application. In such instances, the patient's head is effectively pushed towards the fixed side of the support and fixation structure. Where a head support or cushion is used, like head cushion (1518), the patient's head is pushed against the fringe or edge of the head support cushion's indentation where the head would typically be received when not in a fixed position. This uneven or highly directional application of force from one side can lead to significantly higher contact pressure in this area near the head cushion, causing a pressure ulcer.

As mentioned above, with HFD (1500) described above, with the two extension bar (1522) configuration, the pads (1514) can be positioned with an equal distance to the head resting on the head cushion (1518). The fluid chambers (1554) of the pads (1514) are interconnected via the hose (1556), so the pressure on the head from both sides is equal. This combination leaves the head in a centered position on the main head cushion (1518), which may also be referred to as the head support cushion from time to time.

In the present example, but not required in all examples, the entire support assembly (1512), including the torque screw (1538) and locking bolt (1550) is radiolucent. In this manner, the entire support assembly (1512) may be produced from synthetic materials to achieve radiolucency.

A. Exemplary Pads

Figure 20:
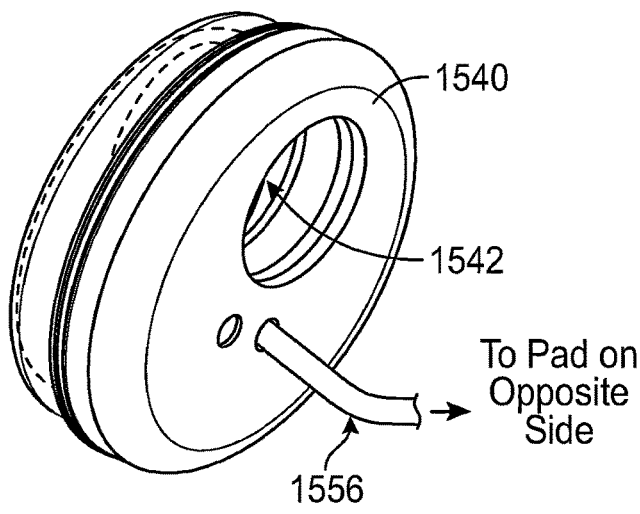
FIG. 20 depicts a perspective view of a pad of the HFD of FIG. 13.
Figure 21:
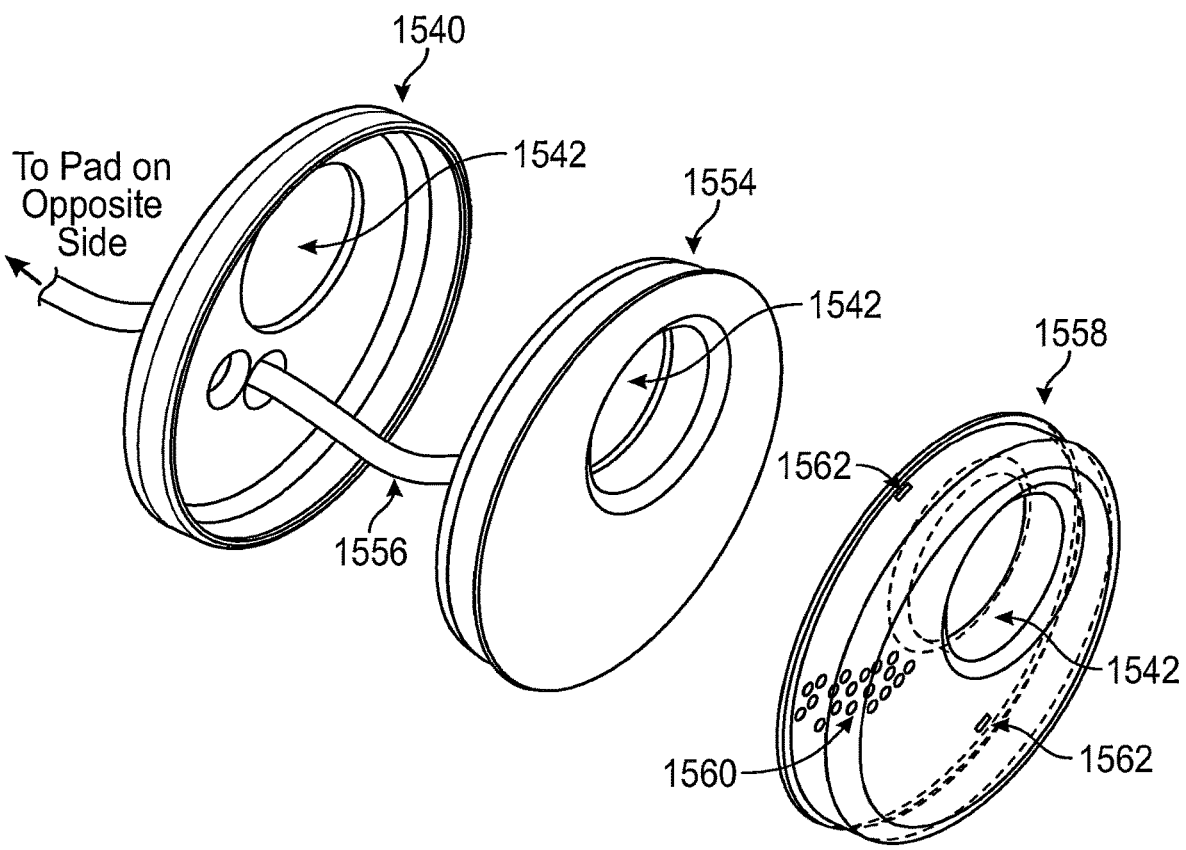
FIG. 21 depicts an exploded perspective view of the pad of FIG. 20.

In the present version, each pad (1514) is made of a synthetic material, which in some instances may be referred to as a foil. As best seen in FIGS. 20 and 21, the pad (1514) is configured with two separated chambers that provide two layers between the support assembly (1512) and the patients' head. The first chamber (1554) is a fluid chamber. The fluid chamber (1554) is fillable with air in the present example, but other fluids, including liquids may be used in other versions. The fluid chamber (1554) is located between the support assembly (1512) and the second chamber (1558), which is filled with granular material. The granular material chamber (1558) is positioned such that in use it will contact the patient (1560). In use, the fluid chamber (1554) is configured to be filled to push the granular material chamber (1558) against the patient's head.

In the present example, the granular material (1560) within the granular material chamber (1558) comprises granule of expanded polystyrene, sometimes referred to as EPS granules. The granular material chamber (1558) comprises small holes or vents (1562) in the outer material defining the chamber (1558). These small holes (1562) may be nearby the seam or along the edges so as to not be blocked or closed-off by the contact between the chamber (1558) and the head of the patient. When the fluid chamber (1554) is empty, there is air in between the EPS granules within the second chamber (1558). When stabilizing a head of a patient, the pads (1514) are positioned between the patient's head and the support assembly (1512). By filling the fluid chamber (1554), pressure is applied by the fluid chamber (1554) to the granular material chamber (1558), thereby squeezing out the air between the EPS granules, which escapes through the holes or vents (1562). Thereby the EPS granules are pressed together and align or conform to the head shape of the patient. In this manner, the pressure applied to the patient's head is distributed homogenously and correlates with the pressure inside the fluid chamber (1554). As mentioned above, the fluid chambers (1554) of each pad (1514) on each side of the support assembly (1512) are connected by a hose (1556), leading to an equal pressure level in both pads (1514). In the present example, a hand pump (1564) is connectable to the hose (1556) in order to apply pressure to the fluid chamber (1554) of each pad (1514). The pump (1564) also offers a release valve (1566) to relieve the pressure from the fluid chambers (1554).

With the above described configuration, in addition to providing even or homogenous distribution of contact pressure with the patient's head, the HFD (1500) provides a high level of stability. For instance, HFD (1500) can provide non-invasive stabilization up to about 12 hours within pressure indication, e.g. via the scale on the torque screw (1538) or via a gauge (1568) on the hand pump (1564). Prior to this development, long term stabilization of a patient's head with a pressure indication means has used invasive pinning techniques.

The pad (1514), in one version, is constructed such that fluid chamber (1554) and granular material chamber (1558) are separate chambers, but sealed together as a single pad. In this version, the pad (1514) may include a membrane positioned between the chambers (1554, 1558), although the membrane is not required in all versions.

In another version, the pad (1514) is constructed such that each chamber (1554, 1558) is separable form the other. In this manner the pad (1514) is constructed of two separate pads that correspond to each chamber (1554, 1558), and that are used together as a kind of pad assembly. With this configuration for the pad (1514), the granular material chamber (1558) that contacts the patient can be a single-use disposable product or component, while the fluid chamber (1554) can be reprocessed and reused. Reprocessing of fluid chambers (1554) of pads (1514) may be achieved with automated cleaning or manual cleaning, for example. Similarly, the support assembly (1512) of the non-invasive, radiolucent HFD (1500) is suitable for automated cleaning and disinfection, as well as steam sterilization.

B. Exemplary Pressure Application and Indication

Irrespective of whether the pad (1514) uses joined or combined chambers (1554, 1558) in a single pad configuration, or the pad (1514) uses separable chambers (1554, 1558) in a multi pad configuration, pressure application and force indication with the HFD (1500) may be achieved using the torque screw (1538) and/or using the hand pump (1564) with the pressure gauge (1568).

Figure 22:
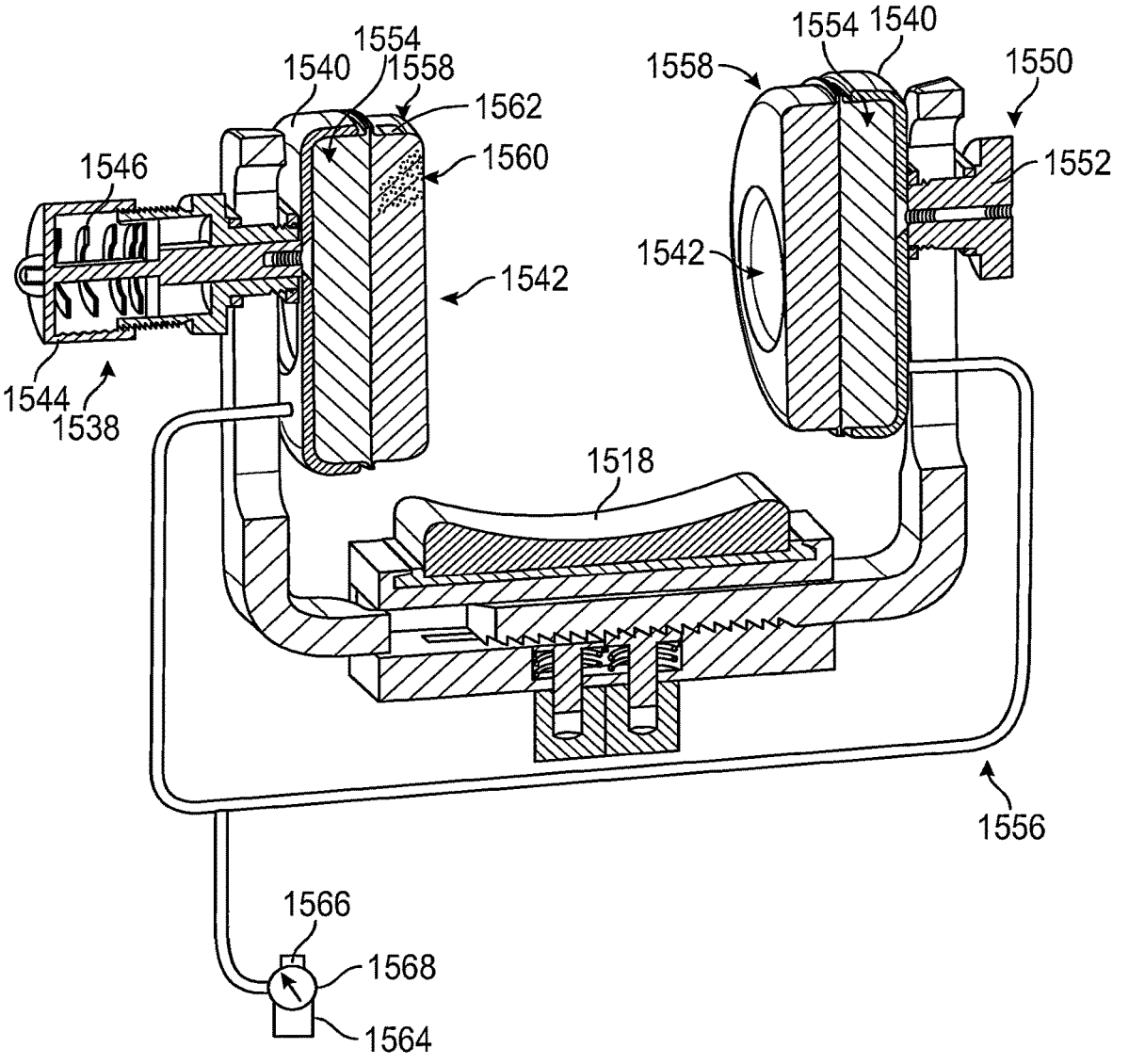
FIG. 22 depicts a cross-sectional view of the HFD of FIG. 13, shown assembled with the pump.

When using the torque screw (1538), the fluid chambers (1554) of each pad (1514) connected with the respective extension bar (1522) are connected by the hose (1556) and pre-filled with air or other fluid before use, as shown in FIG. 22. The torque screw (1538) is mounted at the support assembly (1512) to push the pad (1514) towards the patient's head and thereby increase the pressure inside the fluid chamber (1554). The applied pressure is displayed to the user by the scale (1548) at the torque screw (1538).

When pre-filling the fluid chambers (1554) the pre-filling can be accomplished in a variety of ways. In one example, fluid chambers (1554) are pre-filled during manufacturing such that the pads (1514) are delivered with fluid chambers (1554) pre-filled. In this example, the fluid chambers (1514) of two pads (1514) have the hose (1556) connecting them but the fluid chambers (1554) and hose (1556) are sealed such that no additional fluid is added or removed. In this example, when the pressure is increased or decreased based on the tightening of the torque screw (1538) and compression of the pads (1514) against the patient's head.

In another example of pre-filling the fluid chambers (1554), the hose (1556) connecting two fluid chambers (1554) can have a port that permits connection with the hand pump (1564). The hand pump (1564) in this example may or may not have the gauge (1568). Still in another example, the hose (1556) can have a port that may connect with a large syringe for pre-filling with air or fluid. In some examples for pre-filling, the port that provides access for receiving air or fluid may be included on the hose (1556) as described above, or the port could be included on one or more of the fluid chamber (1554) of the pads (1514). In some examples, the port comprises a valve that selectively seals the fluid chambers (1554). In some instances the valve may be a one-way valve that allows air or fluid to be added to the fluid chambers (1554) but not removed.

Alternatively or in addition to the use of the torque screw (1538) for pressure application and force indication, such pressure application and force indication may be achieved by connecting the hand pump (1564) having the pressure gauge (1568) with the fluid chambers (1554) either directly or indirectly via the hose (1556). In this example, pre-filling can be done but is not required as the fluid chambers (1554) can be filled during use. In this configuration, the two fluid chambers (1554) of the pads (1514) connected by the hose (1556), and with the hand pump (1564) having the pressure gauge (1568) give the user feedback about the applied contact pressure. The contact pressure in this regards represents the surface pressure applied by the pads (1514) on the patient's head and this contact pressure correlates with the pressure within the fluid chambers (1554). In some versions, the pressure gauge (1568) of the hand pump (1564) is calibrated to indicate the contact pressure at the interface between the patient's head and the pads (1514) as opposed to indicating the of the fluid chambers (1554) themselves. In other versions, the pressure gauge (1568) can be configured to indicate the pressure of the fluid chambers (1554) themselves with a correlation of that indication to the contact pressure being made thereafter by manual or automated correlations. Similarly, in versions using the torque screw (1538), the scale (1548) may be configured to correlate with the contact pressure.

In one example using the hand pump (1564), the gauge (1568) is configured to provide the user with a general indication of acceptable pressure ranges. These may be indicated by colored bands on the pressure gauge (1568) as opposed to finite numbers or pressure readings. For instance, the pressure gauge (1568) can comprise a green band or zone followed by an adjacent red band or zone. When a needle of the pressure gauge (1568) points anywhere within the green band then an appropriate amount of pressure is being used. In this sense the appropriate amount of pressure is one that provides the desired stabilization benefits while not being too great to cause harm or injury to the patient. In this example, if the needle of the pressure gauge (1568) falls within a red band then the pressure may be too great and put the patient at an unacceptable level of risk for injury. Also in this example, another color band, e.g. white or yellow, may be presented that represents a condition where the pressure is too low such that the desired stabilization may not be achieved. The hand pump (1564) may be configured with different gauges (1568) based on the particular patients and/or procedures, or different hand pumps (1564) could be used altogether. For instance, the hand pump (1564) could be configured with one gauge (1568) when used with pediatric patients, but with another gauge when used with adult patients. The gauges may have differently calibrated colored bands based on the type of patient and/or procedure requirements.

In some versions, the HFD (1500) is configured such that the pressure can be adjusted when the HFD (1500) is in use. For instance, in the versions that include the hand pump (1564) connectable with the fluid chambers (1554) directly or indirectly via the hose (1556), the hand pump (1564) may be accessible to add fluid to or remove fluid from the fluid chambers (1554) during a procedure. In some cases the hand pump (1564) may include an extension conduit that connects the hand pump (1564) with the fluid chambers (1554) directly or indirectly via the hose (1556) while allowing for the hand pump (1564) to be located some distance away from the HFD (1500). This can be to relocate the hand pump (1564) from beneath surgical drapes so it can be easily accessed during a procedure without disturbing such surgical drapes or other equipment or accessories that may be used with HFD (1500).

In versions that use the torque screw (1538) for pressure application and indication, pressure may also be adjusted when the HFD (1500) is in use by accessing the handle (1544) of the torque screw (1538) and adjusting the torque screw (1538) by rotating the handle (1544). In some instances, the torque screw (1538) may be beneath a surgical drape and accessing the torque screw (1538) may require temporary removal or relocating of the surgical drape.

While some of the above examples describe the use of the hand pump (1564), it will be apparent to those of ordinary skill in the art in view of the teachings herein, that in some other versions, the hand pump (1564) may be replaced by an automated pump and even a pumping system having control features to set, monitor, and maintain a desired pressure.

With HFD (1500) as described above, the support assembly (1512) and pads (1514) minimize migration of the head position. For instance, the pad (1514) characteristics described above plus the stiffness of the extension bars (1522) and clamp structure promote this minimization of head position migration. This in turn allows HFD (1500) to provide a non-invasive head stabilization structure that can be used with intraoperative navigation techniques. By way of example and not limitation, the HFD (1500) is suitable for electromagnetic navigation, like e.g. Brainlab Kick EM. Additionally, the combination of long-term, non-invasive head stabilization and radiolucency allows for intra-operative imaging (CT, MRI, sonography).

In use when stabilizing the head of a patient using the HFD (1500), first the head is supported from beneath by head cushion (1518) and base assembly (1516). Next, extension bars (1522) are adjusted around the perimeter of the base assembly (1516) by advancing the extension bars (1522) toward the central axis (A1) of the HFD (1500). Then, slides (1530) and pads (1514) are adjusted to contact the patient's head in a desired fashion, e.g. compensating or aligning for the patient's ear. With the slides (1530) tight and the pads (1514) fixed, in versions of the HFDs where only one or more torque screws (1538) are used for pressure application and indication, the one or more torque screw (1538) are tightened down such that the fluid chambers (1554) are advanced toward the granular material chambers (1558) to promote the pads (1514) conforming to the patient's head. In versions of the HFDs where the pump (1564) is used for pressure application and indication, the pump (1564) is actuated to add air or fluid to the fluid chambers (1554), which then causes the fluid chambers (1554) to advance toward the granular material chambers (1558) to promote the pads (1514) conforming to the patient's head as described above. Once the pads (1514) are positioned and conforming to the patient's head, adjustments can be made to the torque screw (1538) and/or via the hand pump (1564) as the case may be depending on the HFD configuration or version to achieve the desired level of contact pressure with the patient for stabilization of the head.

All of the above steps in an exemplary stabilization method are not required in all stabilizations procedures. In some cases one or more adjustments may be omitted, and or other steps may be included. Similarly, the adjustments may be made in sequences other than the one described in the example procedure above. In view of the teachings herein, other procedures for supporting and stabilizing a patient's head using any of the HFDs described herein will be apparent to those of ordinary skill in the art.

Figures 23, 24:
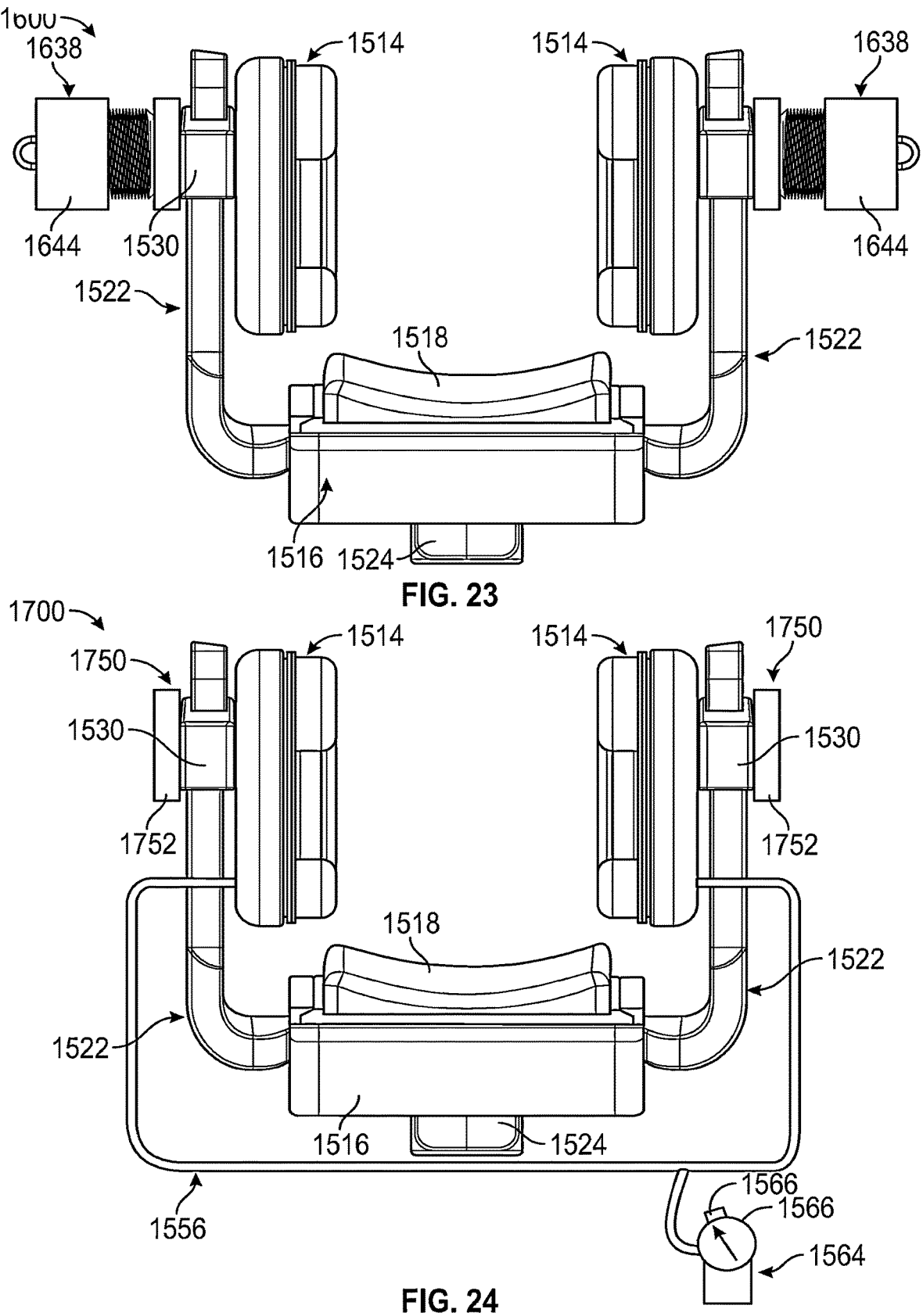
FIG. 23 depicts a front view of another exemplary HFD configured as a non-invasive HFD with a torque screw on each extension bar.
FIG. 24 depicts a front view of another exemplary HFD configured as a non-invasive HFD with a locking bolt on each extension bar.

Other HFDs, or modified versions of HFD (1500) are shown in FIGS. 23 and 24 as HFD (1600) and HFD (1700). HFD (1600) is configured the same or similar to HFD (1500) as described above, except HFD (1600) comprises two torque screws (1638), one for each pad (1514). With this configuration, the HFD (1600) omits the hose (1556) between the two fluid chambers (1554) of the pads (1514). As described above, with this configuration for the HFD (1600) the pads (1614) would be pre-filled with fluid during manufacturing and sealed.

The HFD (1700) is configured the same or similar to HFD (1500) as described above, except HFD (1700) omits the torque screw altogether and instead includes two locking bolts (1750), one for each pad (1514). With this configuration, the pressure application and indication is accomplished with the pump (1564) that supplies air or fluid to the fluid chambers (1554) of the respective pads (1514) and the gauge (1568) of the pump (1564). In the same manner as described above with respect to the HFD (1500), with the HFD (1700) the pump (1564) is connectable with the fluid chambers (1554) directly or indirectly via the hose (1556). Furthermore the operability of the pump (1564) and the gauge (1568) is the same with the HFD (1700) as is described above with respect to those instances where HFD (1500) uses the pump (1564) and the gauge (1568).

In view of the teachings herein, other various ways to modify any of the HFDs (1500, 1600, 1700) or components thereof will be apparent to those of ordinary skill in the art in view of the teachings herein. For instance, in some versions, the HFDs (1500, 1600, 1700) may incorporate any of the central head supports (700, 1310, 1410) and/or positioning assembly (900) described above.

VI. Exemplary Non-Invasive Head Fixation Device with Multi-Chambered Pads

Figure 25:
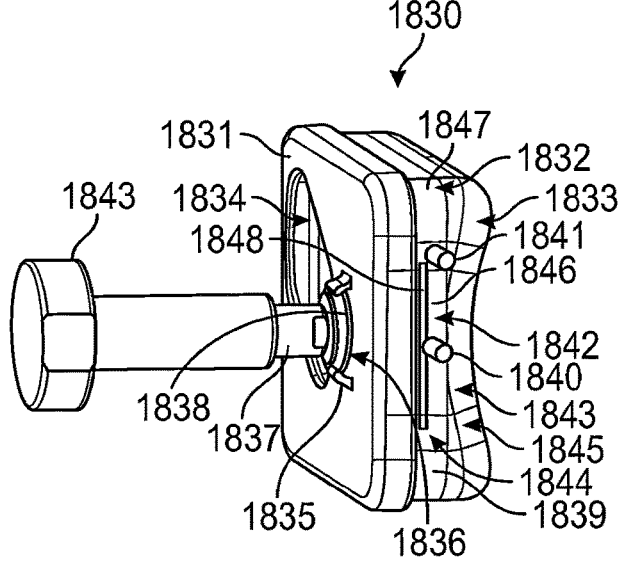
FIG. 25 depicts a perspective view of another exemplary pair of stabilization assemblies usable with the HFD of FIG. 1.
Figure 25:
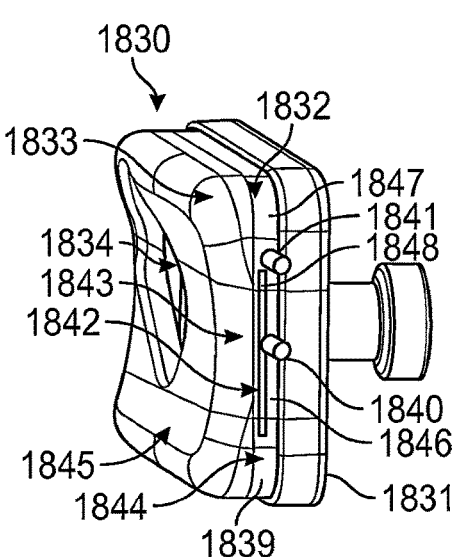

FIG. 25 depicts multi-chamber pads (1830) for the stabilization assemblies (816) to provide for a non-invasive stabilization with any of the HFDs (600, 1500, 1600, 1700) described above. Each pad (1830) comprises a multi-chamber structure with a first chamber (1832) having an internal space (1847) that is configured to be filled with a fluid. The fluid may be a gas or a liquid. The first chamber (1832) includes a port (1841) that is configured to provide access to the internal space (1847). The fluid may be directed to the internal space (1847) within the first chamber (1832) or extracted from or vented from the internal space (1847) of the first chamber (1832). When venting fluid from the first chamber (1832), all or a portion of the fluid may be released or vented from the internal space (1847). Each pad (1830) further comprises a second chamber (1844) having an internal space (1839) that is configured to be filled with the fluid, or fluid may be extracted from or vented from the internal space (1839) of the second chamber (1844). When venting fluid from the second chamber (1844), all or a portion of the fluid may be released or vented from the internal space (1839). In the present example, the internal space (1847) of the first chamber (1832) and the internal space (1839) of the second chamber (1844) are in fluid communication by way of a connection tube (1848) that extends between the internal spaces (1847, 1839) of the first and second chambers (1832, 1844).

Each pad (1830) further comprises a third chamber (1842) positioned between the first and second chambers (1832, 1844). In this configuration, the first and second chambers (1832, 1844) collectively define a pair of outer chambers while the third chamber (1842) defines a middle chamber. The third chamber (1842) also comprises an internal space (1846), and the connection tube (1848) extends through the internal space (1846) of the third chamber (1842). The internal space (1846) of the third chamber (1842) is configured to be filled with the fluid similar to the first and second chambers (1832, 1844). The fluid may be added to or removed from the internal space (1846), which can change the pressure within this area of the pad (1830). The third chamber (1842) comprises a port (1840) similar to the first chamber (1832). The port (1840) provides access to the internal space (1846) and is used to direct fluid to the internal space (1846) or vent fluid from the internal space (1846).

Each pad (1830) further comprises a fourth chamber (1833), a fifth chamber (1845), and a sixth chamber (1843), each configured be filled with a shape-conforming material. The first chamber (1832) is positioned adjacent to the fourth chamber (1833), and the fourth chamber (1833) is configured to contact the head of the patient. The second chamber (1844) is positioned adjacent to the fifth chamber (1845), and the fifth chamber (1845) is configured to contact the head of the patient. The third chamber (1842) is positioned adjacent to the sixth chamber (1843), and the sixth chamber (1843) is configured to contact the head of the patient. In view of the teachings herein, it will be apparent to those of ordinary skill in the art that the relative positions of the first and fourth chambers (1832, 1833), the second and fifth chambers (1844, 1845), and the third and sixth chambers (1842, 1843) may be switched in other versions. In one version, the shape-conforming material within the fourth, fifth, and sixth chambers (1833, 1845, 1843) is one of either a gel, a foam, a granular material or a combination. In view of the teachings herein, other shape-conforming materials usable with the pad (1830) will be apparent to those of ordinary skill in the art.

With the configuration of the pad (1830) described above, the pad (1830) is configured to provide a various pressure profiles depending on the manner of adjustments with the fluid and each of the respective internal spaces (1847, 1846, 1839). For instance, in some versions, a uniform distribution of contact pressure can be achieved where the third chamber (1842) is configured to hold the same amount of fluid per unit of volume within the internal space (1846) as in the internal spaces (1847, 1839) of the first and second chambers (1832, 1844). Still in other versions, the outer chambers may have matching pressures while the middle chamber has a pressure that may be higher or lower than the pressure within the outer chambers. Furthermore, in this configuration with differing pressures between the outer chambers and the middle chamber, the fluid may be vented and/or added in a controlled fashion to provide a way to promote blood flow to an area of the patient's tissue in contact with a portion of the pad (1830) while maintaining secure stabilization of the patient's head. Still other suitable configurations for a multi-chambered pad (1830) will be apparent to one with ordinary skill in the art in view of the teachings herein.

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A medical device for supporting and stabilizing a head of a patient during a medical procedure is configured to prevent slippage during supporting and stabilizing the head of the patient. The medical device comprises: (a) a central head support configured to connect with an operating table directly or indirectly via one or more intermediate structures, wherein the central head support is further configured to provide subjacent support to the head of the patient, wherein the central head support comprises a cushion configured to contact the head of the patient; (b) a positioning assembly connectable with the central head support; and (c) a skull clamp configured to adjustably connect with the positioning assembly such that the skull clamp is translatable relative to the positioning assembly, and wherein the skull clamp is further rotatable relative to the central head support, wherein the translation and rotation of the skull clamp permits changing a position of the skull clamp relative to the cushion of the central head support.

Example 2

The medical device of Example 1, wherein the skull clamp comprises a cassette, and wherein the positioning assembly comprises a cassette carrier configured to receive the cassette, wherein the cassette is selectively translatable relative to the cassette carrier to adjust a position of the skull clamp relative to the cassette carrier.

Example 3

The medical device of Example 2, wherein the skull clamp comprises a pair of extension bars received by the cassette, wherein each extension bar is independently moveable relative to the cassette and each other, and independently lockable with the cassette to selectively secure each extension bar with the cassette, wherein each extension bar comprises an upper end portion configured to receive a stabilizing assembly configured to contact the head of the patient and provide lateral support and stabilization to the head of the patient.

Example 4

The medical device of any one or more of Examples 2 through 3, wherein the cassette carrier is rotatably adjustable to change the position of the skull clamp relative to the central head support.

Example 5

The medical device of any one or more of Examples 2 through 4, wherein the cassette comprises a toothed rack and the cassette carrier comprises a locking insert configured to selectively engage with the toothed rack to secure the position of the cassette relative to the cassette carrier.

Example 6

The medical device of any one or more of Examples 2 through 5, wherein the positioning assembly comprises a connector configured to receive the cassette carrier, wherein the cassette carrier is selectively rotatably and translationally adjustable relative to the connector.

Example 7

The medical device of Example 6, wherein the connector is configured to connect with the central head support.

Example 8

The medical device of any one or more of Examples 2 through 5, wherein the positioning assembly comprises a connector and an actuator, wherein the actuator is configured to selectively secure: (a) the translational position of the cassette relative to the cassette carrier; (b) the rotational position of the cassette carrier relative to the connector; and (c) the translational position of the cassette carrier relative to the connector.

Example 9

The medical device of any one or more of Examples 2 through 5, wherein the central head support comprises a slot, wherein a connector of the positioning assembly is receivable within the slot and adjustable along or parallel to a first plane defined by the central head support that extends subjacent to the head of the patient when the head of the patient is supported by the central head support to change a position of the positioning assembly relative to the central head support.

Example 10

The medical device of any one or more of Examples 3 through 9, wherein the upper end portion of each extension bar comprises a bore configured to receive the stabilizing assembly, and wherein the bore of each upper end portion of each extension bar aligns with each other when the cassette receives each of the extension arms of the pair of extension arms.

Example 11

The medical device of any one or more of Examples 3 through 9, wherein the upper end portion of each extension bar comprises a bore configured to receive the stabilizing assembly, and wherein the bore of each upper end portion of each extension bar defines a common axis that extends through a center of the bore of each upper end portion of each extension bar.

Example 12

The medical device of any one or more of Examples 3 through 11, wherein each extension bar defines a longitudinal axis extending along an upright portion of the extension bar from a base of the extension bar, wherein a bore of each extension bar is offset from the longitudinal axis defined by each respective extension bar.

Example 13

The medical device of any one or more of Examples 3 through 12, wherein the pair of extension bars are interchangeable with one another from side to side.

Example 14

The medical device of any one or more of Examples 6 through 8, wherein a combination of rotational adjustment of the cassette carrier relative to the connector and translational adjustment of the cassette relative to the cassette carrier alters a position of the skull clamp substantially concentrically about the head of the patient.

Example 15

The medical device of any one or more of Examples 6 through 8, wherein a combination of rotational adjustment of the cassette carrier relative to the connector and translational adjustment of the cassette relative to the cassette carrier alters a position of the skull clamp about a longitudinal axis of the patient, which extends from the head of the patient to a foot of the patient.

Example 16

The medical device of any one or more of Examples 6 through 8, wherein a combination of rotational adjustment of the cassette carrier relative to the connector and translational adjustment of the cassette relative to the cassette carrier permits semi-lateral positioning of the skull clamp on either side of the head of the patient supported by the central head support up to about forty-five degrees.

Example 17

The medical device of any one or more of Examples 1 through 16, wherein the cushion of the central head support comprises a first chamber, wherein the first chamber comprises an internal space configured to be filled with a fluid, wherein the first chamber comprises a port configured to provide access to the internal space, wherein the first chamber is further configured to be vented to release all or a portion of the fluid from the internal space.

Example 18

The medical device of Example 17, wherein the cushion of the central head support further comprises a second chamber configured to be filled with a shape-conforming material, wherein the first chamber is positioned subjacent to the second chamber, and wherein the second chamber is configured to contact the head of the patient.

Example 19

The medical device of any one or more of Examples 1 through 18, wherein the central head support further comprises a base connected with the cushion, wherein the base comprises a connection member defining an axis extending transversely across the base, wherein the base is pivotable about the axis defined by the connection member to pivotably adjust the orientation of the cushion.

Example 20

The medical device of any one or more of Examples 1 through 16, wherein the cushion of the central head support comprises: (a) a first chamber, wherein the first chamber comprises a first internal space; (b) a second chamber, wherein the second chamber comprises a second internal space, wherein the first internal space and second internal space are in fluid communication by way of a first connection tube extending therebetween such that a pressure within the first and second chambers is the same, wherein the first chamber comprises a first port configured to provide access to the first and second internal spaces, wherein the first and second chambers are configured to be filled with a fluid via the first port, or to be vented to release all or a portion of the fluid; and (c) a third chamber positioned between the first and second chambers such that the first and second chambers collectively define a pair of outer chambers while the third chamber defines a middle chamber, wherein the third chamber comprises a third internal space, wherein the first connection tube extends through the third internal space, wherein the third chamber comprises a second port configured to provide access to the third internal space, wherein the third chamber is configured to be filled with the fluid via the second port, or to be vented to release all or a portion of the fluid.

Example 21

The medical device of Example 20, further comprising: (a) a fourth chamber configured be filled with a shape-conforming material, wherein the first chamber is positioned subjacent to the fourth chamber, and wherein the fourth chamber is configured to contact the head of the patient; (b) a fifth chamber configured be filled with the shape-conforming material, wherein the second chamber is positioned subjacent to the fifth chamber, and wherein the fifth chamber is configured to contact the head of the patient; and (c) a sixth chamber configured be filled with the shape-conforming material, wherein the third chamber is positioned subjacent to the sixth chamber, and wherein the sixth chamber is configured to contact the head of the patient.

Example 22

The medical device of any one or more of Examples 20 through 21, wherein the outer chambers and the middle chamber are configured to be pressurized and de-pressurized in an alternating manner by alternating filling and venting cycles between the outer chambers and the middle chamber.

Example 23

The medical device of any one or more of Examples 1 through 2, wherein: (a) the skull clamp comprises a pair of extension bars, each extension bar comprising an upper end portion configured to receive a stabilizing assembly configured to contact the head of the patient and provide lateral support and stabilization to the head of the patient; and (b) the stabilizing assembly received by each extension bar comprises a pad having a seventh chamber, wherein the seventh chamber comprises a fourth internal space configured to be filled with the fluid, wherein the seventh chamber comprises a third port configured to provide access to the fourth internal space, wherein the seventh chamber is further configured to be vented to release all or a portion of the fluid from the fourth internal space.

Example 24

The medical device of Example 23, wherein the fourth internal space of the pad of each extension bar is in fluid communication with the other pad via a second connection tube that connects the third port of the pad of each extension bar to maintain equal pressure within the seventh chamber of the pad of each extension bar.

Example 25

The medical device of any one or more of Examples 23 through 24, wherein the pad of each extension bar further comprises an eighth chamber configured to be filled with the shape-conforming material, wherein the eight chamber is positioned adjacent to the seventh chamber, and wherein the eighth chamber is configured to contact the head of the patient.

Example 26

A system for stabilizing a head of a patient and reducing patient tissue trauma due to prolonged blood flow reduction to an area of tissue contacted by a stabilization device, wherein the system comprises: (a) a central head support configured to connect with an operating table directly or indirectly via one or more intermediate structures, wherein the central head support is further configured to provide subjacent support to the head of the patient; (b) a positioning assembly connectable with the central head support; (c) a skull clamp configured to adjustably connect with the positioning assembly such that the skull clamp is translatable relative to the positioning assembly, and wherein the skull clamp is further rotatable relative to the central head support, wherein the translation and rotation of the skull clamp permits changing a position of the skull clamp relative to the central head support; (d) a cushion of the central head support, wherein the cushion is configured to contact the head of the patient, and wherein the cushion comprises one or more chambers, wherein the one or more chambers each comprise an internal space configured to be filled with a fluid, or to be vented to release all or a portion of the fluid; (e) a pump, wherein the pump is configured to supply the fluid to the one or more chambers; (f) one or more pressure sensors in communication with the respective one or more chambers; (g) one or more valves in fluid communication with the pump and the respective one or more chambers, wherein the one or more valves is operable to permit the fluid to flow from the pump into the respective one or more chambers; and (h) a control unit connected with the pump, the one or more pressure sensors, and the one or more valves, wherein the control unit is configured to operate the pump to supply the fluid to the one or more chambers.

Example 27

The system of Example 26, wherein the one or more chambers comprise two or more chambers, wherein the control unit executes an alternating vent and fill cycle, wherein the two or more chambers are vented and filled in an alternating manner whereby at least one of the two or more chambers is vented and its pressure reduced. Furthermore, where the procedure uses or requires navigation, at least one of the two or more chambers remains at initial dimensions by means of fluid control, to avoid a migration of the patients' head when other chambers are vented and pressure is reduced.

Example 28

A system for stabilizing a head of a patient and reducing patient tissue trauma due to prolonged blood flow reduction to an area of tissue contacted by a stabilization device, wherein the system comprises: (a) a central head support configured to connect with an operating table directly or indirectly via one or more intermediate structures, wherein the central head support is further configured to provide subjacent support to the head of the patient; (b) a positioning assembly connectable with the central head support; (c) a skull clamp configured to adjustably connect with the positioning assembly such that the skull clamp is translatable relative to the positioning assembly, and wherein the skull clamp is further rotatable relative to the central head support, wherein the translation and rotation of the skull clamp permits changing a position of the skull clamp relative to the central head support; (d) a cushion of the central head support, wherein the cushion is configured to contact the head of the patient, and wherein the cushion comprises: (i) a first chamber, wherein the first chamber comprises a first internal space, (ii) a second chamber, wherein the second chamber comprises a second internal space, wherein the first and second chambers are configured to be filled with a fluid, or to be vented to release all or a portion of the fluid, and (iii) a third chamber positioned between the first and second chambers such that the first and second chambers collectively define a pair of outer chambers while the third chamber defines a middle chamber, wherein the third chamber comprises a third internal space, wherein the third chamber is configured to be filled with the fluid, or to be vented to release all or a portion of the fluid; (e) a pump, wherein the pump is configured to supply the fluid to one or more of the first, second, and third chambers of the cushion; (f) a first pressure sensor in communication with the first chamber; (g) a second pressure sensor in communication with the third chamber; (h) a first valve in fluid communication with the pump and the first chamber, wherein the first valve is operable to permit the fluid to flow from the pump into the first chamber; (i) a second valve in fluid communication with the pump and the third chamber, wherein the second valve is operable to permit the fluid to flow from the pump into the third chamber; and (j) a control unit connected with the pump, the first and second pressure sensors, and the first and second valves, wherein the control unit is configured to operate the pump to supply the fluid to the one or more of the first, second, and third chambers of the cushion.

Example 29

The system of any Example 28, wherein the first internal space and second internal space are in fluid communication by way of a first connection tube extending therebetween such that a pressure within the first and second chambers is the same, wherein the first chamber comprises a first port configured to provide access to the first and second internal spaces, wherein the first and second chambers are configured to be filled with the fluid via the first port, wherein the third chamber comprises a second port configured to provide access to the third internal space, wherein the third chamber is configured to be filled with the fluid via the second port.

Example 30

The system of any one or more of Examples 28 through 29, wherein the control unit executes an alternating vent and fill cycle, wherein the pair of outer chambers and the middle chamber are vented and filled in an alternating manner.

Example 31

The system of Example 30, wherein the control unit monitors the first and the second pressure sensors to ensure that a select one or both of a first pressure within the pair of outer chambers and a second pressure within the middle chamber are at a predetermined setpoint before commencing a repeat of the alternating vent and fill cycle such that the head of the patient maintains position during the alternating vent and fill cycle.

Example 32

A system for stabilizing a head of a patient and reducing patient tissue trauma due to prolonged blood flow reduction to an area of tissue contacted by a stabilization device comprises a central head support configured to connect with an operating table directly or indirectly via one or more intermediate structures. The central head support is further configured to provide subjacent support to the head of the patient. The system further comprises a skull clamp configured to connect directly or indirectly with the central head support, and a cushion configured to connect directly or indirectly with the central head support, wherein the cushion is configured to contact the head of the patient, and wherein the cushion comprises one or more chambers. The one or more chambers each comprise an internal space configured to be filled with a fluid, or to be vented to release all or a portion of the fluid. The system further comprises a pump, wherein the pump is configured to supply the fluid to the one or more chambers, and one or more valves in fluid communication with the pump and the respective one or more chambers, wherein the one or more valves is operable to permit the fluid to flow from the pump into the respective one or more chambers.

Example 33

The system of Example 32, wherein the one or more valves comprise one valve, and wherein the one or more chambers comprise two or more chambers. The valve is in fluid communication with the respective two or more chambers, and the valve is configurable to permit fluid flow to the two or more chambers independent from one another.

Example 34

The system of any one or more of Examples 32 through 33, wherein the one or more valves is/are further configurable to permit fluid venting from the two or more chambers independent from one another.

Example 35

The system of any one or more of Examples 32 through 34, wherein two or more chambers comprise a middle chamber and a pair of outer chambers, wherein in a first state a pressure within the middle chamber and the pair of outer chambers is substantially equal, wherein in a second state the pressure within the middle chamber is decreased by the valve venting fluid from the middle chamber, and wherein in a third state the pressure within the middle chamber is increased by the valve directing fluid to the middle chamber.

Example 36

The system of Example 35, wherein in the third state the pressure within the middle chamber and the pair of outer chambers is substantially equal.

Example 37

The system of any one or more of Examples 35 through 36, wherein in the second state the pressure within the pair of outer chambers increases relative to the pressure within the pair of outer chambers in the first state, wherein a volume of fluid within the pair of outer chambers remains constant from the first state to the second state.

Example 38

A head stabilization device for stabilizing a head of a patient comprises (a) a base assembly configured to support the head of the patient resting thereon; (b) at least two extension bars attachable to the base assembly, wherein the at least two extension bars are adjustable relative to the base assembly and each other to allow changes in the distance between each of the extension bars, wherein the at least two extension bars each comprise a lateral extending portion and an upright extending portion; and (c) at least two pads, each connectable with one of the upright extending portions of each extension bar, wherein the at least two pads are configured to contact the head of the patient, and wherein each pad comprises a fluid-filled chamber and a granular material filled chamber.

Example 39

The device of Example 38, further comprising at least two slides connectable with one of the upright extending portions of each extension bar, wherein the slides are configured to adjust longitudinally along the upright extending portions of the extension bars to position the pads.

Example 40

The device of any one or more of Examples 38 through 39, wherein each of the lateral extending portions of the extension bars comprise a toothed region, and wherein the base assembly comprises at least two release knobs, wherein each release knob is in mechanical communication with a respective one of the extension bars, and wherein each of the release knobs comprise a toothed feature configured to selectively engage with the toothed region of the respective lateral extending portion of the extension bar.

Example 41

The device of any one or more of Examples 38 through 40, wherein the upright extending portions of the extension bars comprise a trapezoidal-shaped cross section configured to receive one or more accessories.

Example 42

The device of any one or more of Examples 38 through 41, further comprising an indication device comprising a force-dependent deformable body, displaying the force applied to the fluid-filled chamber.

Example 43

The device of any one or more of Examples 38 through 42, further comprising an indication device comprising a gauge showing the pressure applied to the fluid-filled chamber.

Example 44

The device of any one or more of Examples 38 through 43, further comprising a head support cushion connectable with the base assembly, wherein the base assembly allows for an adjustment of the head support cushion relative to the base assembly.

Example 45

A head stabilization device for stabilizing a head of a patient comprises (a) a pair of extension bars extending from a base assembly; (b) a pair of ratchet features, wherein each one of the pair of ratchet features is in mechanical communication with one of the pair of extension bars, wherein the ratchet features are configured to selectively adjust the pair of extension bars laterally relative to a central axis of the device; (c) a pair of pads, wherein each one of the pair of pads is connectable with one of the pair of extension bars, wherein each one of the pair of pads comprises a first chamber filled with fluid and a second chamber filled with granular material, wherein the first chamber is configured to impinge upon the second chamber such that the granular material within the second chamber conforms to the head of the patient; and (d) a pressure application and indication feature configured to provide fine adjustment of the contact pressure between the pads and the head of the patient.

Example 46

The device of Example 45, wherein the pressure application and indication feature comprises a torque screw.

Example 47

The device of any one or more of Examples 45 through 46, wherein the pressure application and indication feature comprises a pump with a pressure gauge.

US 12,678,361 B2

39

Example 48

The device of Example 44, wherein the head support cushion comprises a first chamber configured to be filled with a shape-conforming material, and wherein the first chamber is configured to contact the head of the patient.

VIII. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. Patent App. No. 62/662,874, entitled "Head Stabilization System and Method with Arc Features," filed on Apr. 26, 2018, the disclosure of which is incorporated by reference herein. Various suitable ways in which the teachings herein may be combined with the teachings of U.S. Patent App. No. 62/662,874 will be apparent to those of ordinary skill in the art.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A medical device configured for supporting and stabilizing a head of a patient during a medical procedure, the medical device comprising:

(a) a positioning assembly defining an axis of rotation, wherein the positioning assembly includes a selectively rotatable portion that is rotatable about the axis of rotation and is configured to adjust a rotational position of the selectively rotatable portion of the positioning assembly relative to the head of the patient;

(b) a head support configured to directly or indirectly adjustably connect with the positioning assembly such that the head support is translatable independent from and relative to the positioning assembly and rotatable in unison with the selectively rotatable portion of the positioning assembly, wherein the translation and rotation of the head support is configured to permit changing a position of the head support relative to the head of the patient; and (c) a body receivable by the positioning assembly, wherein the body is selectively translatable relative to the selectively rotatable portion of the positioning assembly, wherein a combination of rotational adjustment of the selectively rotatable portion of the positioning assembly and translational adjustment of the body relative to the selectively rotatable portion of the positioning assembly is configured to permit semi-lateral positioning of the head support on either side of the head of the patient.

2. The medical device of claim 1, wherein the head support comprises a first extension bar and a second extension bar, wherein the first and second extension bars are selectively moveable relative to each other.

3. The medical device of claim 2, further comprising two or more stabilizing assemblies connectable with the head support, wherein the two or more stabilizing assemblies each include one or more stabilizing features configured to contact the head of the patient.

4. The medical device of claim 3, wherein each extension bar comprises an upper end portion configured to receive one of the two or more stabilizing assemblies.

5. The medical device of claim 4, wherein the upper end portion of each extension bar comprises a bore configured to receive one of the two or more stabilizing assemblies, and wherein the bore of the upper end portion of the first extension bar aligns with the bore of the upper end portion of the second extension bar when the body receives each of the extension bars.

6. The medical device of claim 5, wherein the bore of each upper end portion of each extension bar defines a common axis that extends through a center of the bore of each upper end portion of each extension bar.

7. The medical device of claim 2, wherein the first and second extension bars are selectively moveable relative to the positioning assembly.

8. The medical device of claim 2, wherein each of the extension bars are interchangeable with one another from side to side.

9. The medical device of claim 1, wherein the positioning assembly comprises a fixed portion configured to receive the selectively rotatable portion, wherein the selectively rotatable portion is selectively rotatably and translationally adjustable relative to the fixed portion of the positioning assembly.

10. The medical device of claim 9, wherein a combination of rotational adjustment of the selectively rotatable portion of the positioning assembly relative to the fixed portion of the positioning assembly and translational adjustment of the body relative to the selectively rotatable portion of the positioning assembly is configured to alter the position of the head support substantially concentrically about the head of the patient.

11. The medical device of claim 1, wherein a first extension bar and a second extension bar are received by the body, wherein each extension bar is independently moveable relative to the body and each other, and independently lockable with the body to selectively secure each extension bar with the body.

12. The medical device of claim 1, wherein the body comprises a toothed rack and is configured to receive a locking insert configured to selectively engage with the toothed rack to secure a position of the body relative to the selectively rotatable portion of the positioning assembly.

13. The medical device of claim 1, wherein the combination of rotational adjustment of the selectively rotatable portion of the positioning assembly and translational adjustment of the body relative to the selectively rotatable portion of the positioning assembly is configured to alter the position of the head support about a longitudinal axis, which is configured to extend from the head of the patient to a foot of the patient.

14. The medical device of claim 1, wherein the semi-lateral positioning of the head support is up to about forty-five degrees.

15. The medical device of claim 1, wherein the head support comprises a skull clamp.

16. The medical device of claim 1, further configured to provide subjacent support to the head of the patient.

17. A medical device configured for supporting and stabilizing a head of a patient during a medical procedure, the medical device comprising:

(a) a positioning assembly defining an axis of rotation, wherein the positioning assembly includes a selectively rotatable portion that is rotatable about the axis of rotation and is configured to adjust a rotational position of the selectively rotatable portion of the positioning assembly relative to the head of the patient;

(b) a head support configured to directly or indirectly adjustably connect with the positioning assembly such that the head support is translatable independent from and relative to the positioning assembly and rotatable in unison with the selectively rotatable portion of the positioning assembly, wherein the translation and rotation of the head support is configured to permit changing a position of the head support relative to the head of the patient; and (c) a body receivable by the positioning assembly, wherein the body is selectively translatable relative to the selectively rotatable portion of the positioning assembly, wherein the positioning assembly comprises a connector and an actuator, wherein the actuator is configured to selectively secure: (a) a translational position of the body relative to the selectively rotatable portion of the positioning assembly; (b) the rotational position of the selectively rotatable portion of the positioning assembly relative to the connector; and (c) a translational position of the selectively rotatable portion of the positioning assembly relative to the connector.

18. A medical device configured for supporting and stabilizing a head of a patient during a medical procedure, the medical device comprising:

(a) a positioning assembly defining an axis of rotation, wherein the positioning assembly includes a selectively rotatable portion that is rotatable about the axis of rotation and is configured to adjust a rotational position of the selectively rotatable portion of the positioning assembly relative to the head of the patient;

(b) a skull clamp configured to directly or indirectly adjustably connect with the positioning assembly such that the skull clamp is translatable independent from and relative to the positioning assembly and rotatable in unison with the selectively rotatable portion of the positioning assembly, wherein the translation and rotation of the skull clamp is configured to permit changing a position of the skull clamp relative to the head of the patient; and (c) a central head support connectable with the positioning assembly, wherein the central head support is configured to provide subjacent support to the head of the patient, wherein the central head support comprises a slot, wherein a connector of the positioning assembly is receivable within the slot and adjustable along or parallel to a first plane defined by the central head support that extends subjacent to the head of the patient when the head of the patient is supported by the central head support to change a position of the positioning assembly relative to the central head support.

* * * * *